(12) United States Patent
Lingren et al.

(10) Patent No.: US 7,152,002 B2
(45) Date of Patent: Dec. 19, 2006

(54) METHOD AND APPARATUS FOR ANALYSIS OF ELEMENTS IN BULK SUBSTANCE

(75) Inventors: Clinton L. Lingren, San Diego, CA (US); David B. Cook, San Diego, CA (US); James F. Miller, Solana Beach, CA (US); Stephen J. Foster, Vista, CA (US)

(73) Assignee: Sabia, Inc., San Diego, CA (US)

( * ) Notice: Subject to any disclaimer, the term of this patent is extended or adjusted under 35 U.S.C. 154(b) by 0 days.

(21) Appl. No.: 10/222,726

(22) Filed: Aug. 16, 2002

(65) Prior Publication Data

US 2003/0225531 A1    Dec. 4, 2003

Related U.S. Application Data

(60) Provisional application No. 60/385,926, filed on Jun. 3, 2002.

(51) Int. Cl.
*G01N 31/00*    (2006.01)
(52) U.S. Cl. .......................................... 702/23; 376/159
(58) Field of Classification Search .................. 702/18, 702/22, 23, 30–32, 124, 189; 250/256, 358.1, 250/359.1, 362, 390.05, 390.04, 393; 175/42
See application file for complete search history.

(56) References Cited

U.S. PATENT DOCUMENTS

| | | | | |
|---|---|---|---|---|
| 3,124,679 A | | 3/1964 | Tittman et al. ............. 250/380 |
| 3,597,596 A | * | 8/1971 | Lawless et al. ............. 250/362 |
| 4,028,267 A | | 6/1977 | Christell et al. .......... 250/359.1 |
| 4,152,596 A | | 5/1979 | Marshall ................... 250/358.1 |
| 4,171,485 A | * | 10/1979 | Marshall ................... 250/359.1 |
| 4,266,132 A | * | 5/1981 | Marshall, III ............. 250/359.1 |
| 4,578,579 A | * | 3/1986 | Dion ........................... 250/256 |
| 4,582,992 A | | 4/1986 | Atwell et al. ............. 250/359.1 |
| 4,597,596 A | * | 7/1986 | Tozer ........................... 285/187 |
| 4,682,043 A | | 7/1987 | Marshall .................. 250/358.1 |
| 4,766,319 A | * | 8/1988 | Regimand .............. 250/390.05 |
| 4,771,642 A | * | 9/1988 | Parth et al. .............. 73/863.52 |
| 4,812,516 A | * | 3/1989 | Maeda ......................... 525/83 |
| 5,002,721 A | * | 3/1991 | Bernard et al. ............. 376/159 |
| 5,033,071 A | * | 7/1991 | Fuller et al. .................. 378/45 |

(Continued)

OTHER PUBLICATIONS

Borsaru and Jecny, "Application of PGNAA for bulk coal samples in a 4pi geometry", Applied Radiation and Isotopes 54, pp. 519-526, 2001.

(Continued)

*Primary Examiner*—Marc S. Hoff
*Assistant Examiner*—Mohamed Charioui
(74) *Attorney, Agent, or Firm*—Knobbe Martens Olson and Bear LLP

(57) ABSTRACT

A substance analyzer utilizing Prompt Gamma Neutron Activation Analysis for identifying characteristics of a substance and method of manufacturing the same are disclosed. The analyzer is small enough to be portable and to allow its use in many applications where current analyzers cannot be utilized. The analyzer uses a neutron radiation source and a gamma-ray detector to activate the sample material and detect the prompt gamma rays emitted by the sample material. A novel housing for such an analyzer and method for making the housing are also described. Novel methods of operating such an analyzer including via a communications network are also disclosed. Also disclosed are data analysis methods that improve the accuracy and sensitivity of the results of such material analysis.

54 Claims, 14 Drawing Sheets

U.S. PATENT DOCUMENTS

| | | |
|---|---|---|
| 5,053,185 A | 10/1991 | Christensen et al. |
| 5,144,140 A * | 9/1992 | Allyson et al. .......... 250/358.1 |
| 5,162,096 A | 11/1992 | Gozani ....................... 376/159 |
| 5,277,263 A * | 1/1994 | Amen ......................... 175/42 |
| 5,343,041 A * | 8/1994 | Ruscev et al. ........... 250/269.6 |
| 5,396,071 A | 3/1995 | Atwell et al. ............ 250/358.1 |
| 5,732,115 A | 3/1998 | Atwell et al. ............... 376/159 |
| 5,825,030 A | 10/1998 | Hurwitz et al. |
| RE36,201 E * | 4/1999 | Miller ................... 250/390.04 |
| 5,948,137 A * | 9/1999 | Pflaum ...................... 75/10.12 |
| RE36,943 E * | 11/2000 | Atwell et al. ............ 250/358.1 |
| 6,176,323 B1 * | 1/2001 | Weirich et al. ............... 175/40 |
| 6,362,477 B1 | 3/2002 | Sowerby et al. |

OTHER PUBLICATIONS

Lim et al., "An on-belt elemental analyser for the cement industry", Applied Radiation and Isotopes 54, pp. 11-19, 2001.

Craven et al., "A single approach to derivative spectroscopy", Spectrochimica Acta., vol. 44A, No. 5, pp. 539-545, 1988.

Ragavan and Woodward, "On-Line Analysis For Phosphate Beneficiation", AIME Regional Phosphate Conference, 1996.

* cited by examiner

METHOD AND APPARATUS FOR ANALYSIS OF ELEMENTS IN BULK SUBSTANCE

RELATED APPLICATIONS

This application claims the benefit U.S. Provisional Application No. 60,385,926, filed Jun. 3, 2002.

BACKGROUND OF THE INVENTION

1. Field of the Invention

The invention relates to bulk material analyzers, and more particularly, to a method and apparatus for determining the compositional elements of bulk materials utilizing one or more neutron sources and one or more radiation detectors.

2. Description of the Related Art

Atomic research has led to many uses of the neutron, including material analysis. When an atom absorbs a neutron, it increases in atomic weight, but at that moment, the chemical properties of the atom do not change, thus forming a new isotope of the same element. When a neutron is absorbed, the absorbing atom emits one or more gamma rays, the number and energies of which are unique to that element. The new isotope may be unstable and seek stability by emitting one or more forms of radiation over a period of time, which may also result in the atom changing to a different element. Every radioactive isotope has a characteristic half-life as it decays to a stable state. An element that has absorbed a neutron can be identified by either the absorption gamma rays that it emits or by the decay-radiation it emits. The latter is normally referred to as neutron activation analysis and the former is often called prompt-gamma, neutron activation analysis (PGNAA).

Since the neutron was discovered, and especially during the period of the 1940s through the 1960s, both prompt and delayed radiation emissions from neutron absorption have been carefully catalogued at laboratories and universities around the world. PGNAA was applied to coal analysis at the U.S. Bureau of Mines in West Virginia (Stuart and Hall, "On Line Monitoring of Major Ash Elements in Coal Conversion Process," Reprint 789671, October 1978, 13th Intersociety Energy Conversion Engineering Conference, Society of Automotive Engineer, Inc. Warrendale, Pa., pp 586–591) and through research sponsored by EPRI during the 1970s and 1980s. Commercial PGNAA analyzers were introduced during the 1970s and 1980s.

Non-homogeneous industrial materials, such as coal, cement ore, bauxite, kaolin, etc. are ideal candidates for PGNAA. The traditional method of determining average elemental composition of such ores includes taking a representative sample to a laboratory, and most material-analysis techniques used in laboratories assume a homogeneous sample and perform one or more surface measurements. However, obtaining a representative sample of a non-homogeneous bulk material is both expensive and time-consuming. A few grams of sample analyzed in a laboratory are estimated to be representative of the total, which may be hundreds of tons of the bulk material. This large discrepancy between the size of the sample and the size of the actual bulk material is a major source of error in such a measurement. In addition, the inherent delay between sampling the material and obtaining a final measurement in this system is typically on the order of hours, which prevents real-time process control that may be desirable due to changes in material composition.

PGNAA can inherently measure material composition throughout a relatively large volume of material because neutrons penetrate matter to a great depth and the resulting prompt gamma rays are of energies high enough to permit them to escape from a substantial depth within the material. When the bulk material is bombarded with the neutron radiation, different characteristic gamma-ray energy spectra are produced from different elements in the bulk material. By processing detected signals indicative of gamma ray energies, a measurement can be made regarding the elemental content of the bulk material. Directing a PGNAA analyzer at a stream of industrial material can allow the full stream to be measured in real time, thus eliminating sampling error, allowing measurement of instantaneous variations in material, and allowing on-line, closed-loop control of material processes based on material composition.

Commercially available PGNAA analyzers are generally too large (typically weighing several tons and occupying more than 20 cubic meters of space) and too expensive (generally in excess of $300,000) to be used in many applications where they could be beneficial. A significant reduction in size and price of an analyzer while maintaining or improving performance as compared with currently available analyzers would therefore be beneficial in the art.

SUMMARY OF THE INVENTION

The systems and methods of the invention have several features, no single one of which is solely responsible for its desirable attributes. Without limiting the scope as expressed by the claims that follow, its more prominent features will now be discussed briefly. After considering this discussion, and particularly after reading the section entitled "Detailed Description of the Invention," one will understand how the features of the system and methods provide several advantages over traditional systems and methods.

One aspect of the invention is a substance analyzer for identifying characteristics of a substance, having a sample volume adapted to contain a sample of the substance, a source adapted to emit neutrons, and a first material adapted to moderate, shield and reflect the neutron radiation, wherein neutrons emitted by the source are absorbed by the sample, and wherein the sample then emits at least one gamma ray. The analyzer also has a gamma radiation detector located adjacent to the sample volume and adapted to develop electrical signals in response to detection of the emitted gamma rays, and has a housing generally adapted to contain the sample volume, the source, the detector, and the material, wherein the housing comprises an outer container and an inner container.

In another aspect, the invention relates to a detector for detecting photons in a bulk material analyzer comprising insulation limiting heat exchange between the detector and the rest of the analyzer and between the detector and the environment.

In yet another aspect, the invention relates to a source holder for a bulk material sample analyzer having an elongated body and multiple receptacles for receiving sources, wherein the receptacles are located adjacent to one another, and further comprising a locking mechanism for locking the source holder in place.

In yet another aspect, the invention relates to a system for analyzing bulk materials comprising a processor, a memory and an analyzer, wherein the processor and memory are adapted to store raw data to the memory for later processing and analysis.

In another aspect, an analyzer is described comprising a load cell for measuring the weight of the sample being analyzed. Some embodiments comprise a rotator to rotate the sample while it is being analyzed, while other embodiments comprise an elevator to displace the sample along the longitudinal axis of the sample volume while the sample is being analyzed.

In yet another aspect, the invention relates to a novel sample holder for use in a bulk material analyzer comprising a tubular container with one open end and one closed end. In some embodiments the container is made of standard ABS or iron pipe.

In still another aspect, a system is described for three-dimensional surveying of a concentration of various elements in the earth, comprising a portable material analyzer adapted to analyze the concentration of elements, a drill adapted to extract a plurality of material samples from the earth, means for correlating material analyses to a respective drill depth of each of the plurality of material samples. Some embodiments further comprise a geographical map adapted to correlate a drill location of each of the plurality samples with a geographical location, and wherein each of the plurality of samples are analyzed to produce a data set representing the concentration of the elements in each of the samples.

In another aspect, a system is described for operating a substance analyzer, comprising a sample analyzer adapted to determine an elemental composition of a bulk substance sample, a computer adapted to process data received from the sample analyzer, a communications network, a plurality of workstations adapted to communicate via the communications network, and a communications server that is responsive to commands from the computer and the workstations, wherein the communications server is adapted to control a plurality of network resources.

Another aspect relates to a method of manufacturing a housing for a real-time nuclear element analyzer comprising forming an inner surface with an inner container having a first diameter, forming an outer surface with an outer container having a second diameter that is larger than the first diameter, and depositing a pourable housing material into a space formed between the inner surface and the outer surface.

Another aspect of the invention relates to a method of removing pulse pileup from a data spectrum collected from a material analyzer, comprising selecting a spectrum of collected data to be analyzed, determining a count rate for the selected spectrum of data calculating a theoretical spectrum of data from the count rate by, assuming the selected spectrum of data was unpiled data, identifying average pileup values from reference sources for that count rate, piling up the selected spectrum to a theoretical piled up spectrum of data using the identified values, subtracting the selected spectrum of data from the theoretical piled up spectrum of data to estimate a theoretical pileup, and subtracting the theoretical pileup from the selected spectrum of collected data.

In another aspect, a method of adjusting gain and an offset from a selected spectrum of data representing the composition of materials in a material sample is described comprising selecting a spectrum of data to be analyzed finding recognizable peaks in the selected spectrum of data, and applying least squares fit to the selected spectrum of data to define gain and offset correction factors for the measured peaks.

Yet another aspect relates to a method of finding a plurality of recognizable data peaks in the analysis of a spectrum of data from a real-time substance analyzer, comprising, determining the instantaneous first derivative over the entire data spectrum to develop a set of derivative results, taking an average of the set of derivative results, selecting and applying a scale factor to the derivative results to develop a scaled spectrum of data, and locating a plurality of peaks by comparing the scaled spectrum of data to the average of the derivative results to develop a peak count.

Another aspect relates to a method of stabilizing the performance of a neutron activation material analyzer used to produce a spectrum of data, comprising, insulating a detector against heat transfer, and lowering an amount of heat generated in the detector, wherein said lowering is accomplished by reducing an excitation energy in the detector and by using low energy consuming electronic components.

Yet another aspect relates to a method of operating a bulk material analyzer with a communication network, comprising, connecting the analyzer to a computer adapted to operate the analyzer and receive and store data from the analyzer, connecting the computer to a communication network, and connecting a plurality of remote units to the communication network, wherein the remote units are capable of transmitting a plurality of command signals to the computer via the communication network and the server, to operate the analyzer.

Another aspect relates to a bulk material analyzer for analyzing material carried on a conveyor having first and second sides, wherein the analyzer comprises at least one neutron radiation source located on the first side and at least one detector located on the first side.

Finally, the invention also relates to a material analyzing system for analyzing a bulk material, comprising an on-line bulk material analyzer, and a sampling mechanism for directing a flow of the bulk material through the on-line bulk material analyzer.

BRIEF DESCRIPTION OF THE DRAWINGS

FIG. 3b is a cross-sectional view of one embodiment of a static sample analyzer taken along line 3b—3b of FIG. 3a.

DETAILED DESCRIPTION OF THE INVENTION

Embodiments of the invention will now be described with reference to the accompanying figures, wherein like numerals refer to like elements throughout. The terminology used in the description presented herein is not intended to be interpreted in any limited or restrictive manner simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

Figure 1:
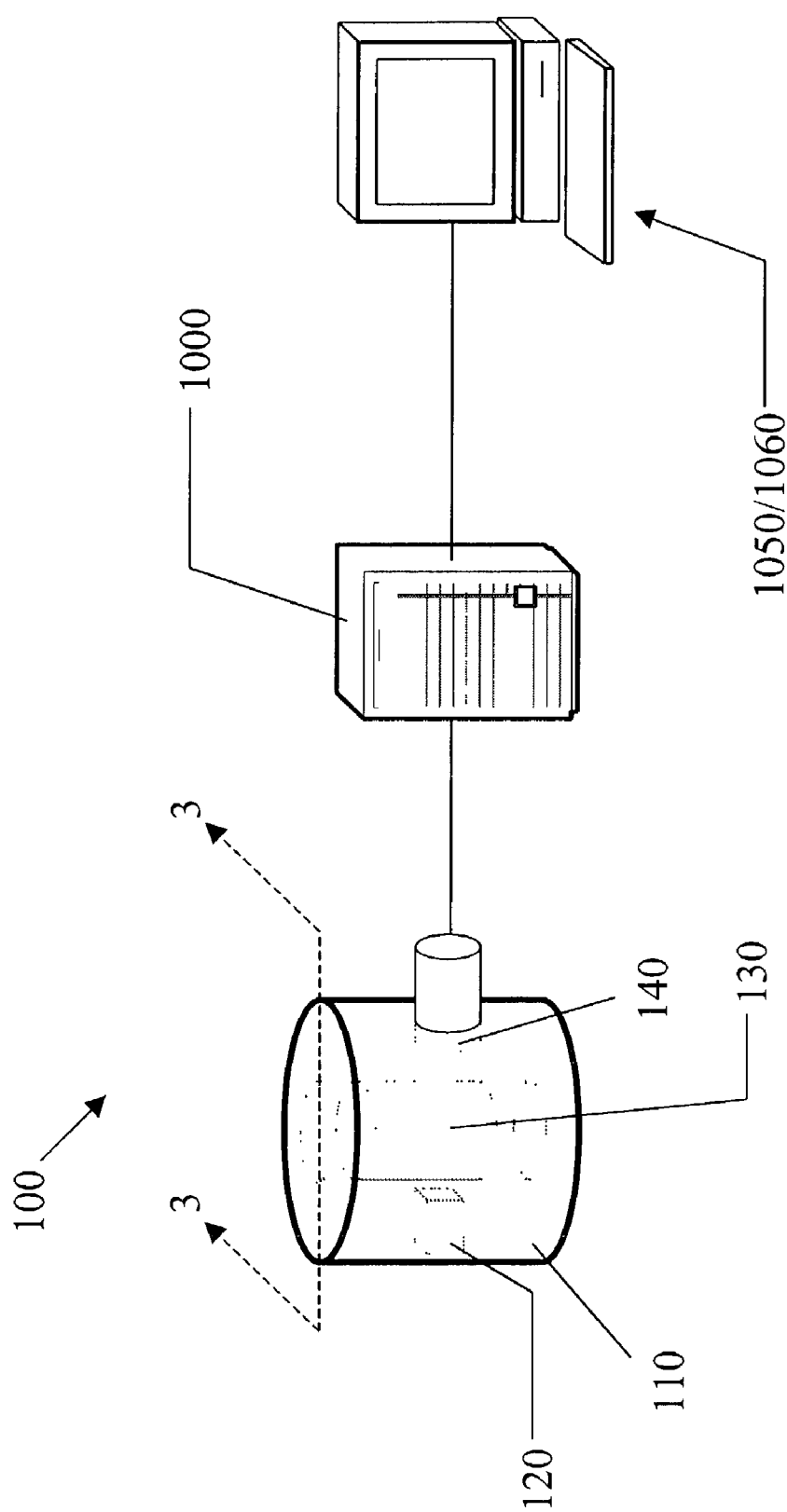
FIG. 1 is a block diagram of one embodiment of a materials analysis system.

Referring initially to FIG. 1, an embodiment of a PGNAA system 100 is illustrated having an analyzer 110 and a computer 1000, or alternatively a data collection and processing device, along with an input/output module 1050/1060 that can provide any sort of output desired or can allow for feedback into the computer 1000 and the analyzer 110, such as for running tests, or for generating test results, or for requesting data analysis, or for any other relevant functionality. In some embodiments the analyzer 110 has a neutron source 120, a sample 130 of bulk material to be analyzed and a detector 140. The neutron source 120 provides neutrons that are absorbed by the various atoms that make up the sample 130, thereby raising the energy level of the nuclei of those absorbing atoms. Each absorbing atom then emits one or more prompt absorption gamma rays, which are characteristic in energy level of their emitting atom, in order to reduce the atom's energy level. The prompt gamma rays are then detected by the detector 140, which in turn develops an electric signal having an energy level characteristic of each detected gamma ray.

The signals generated by the detector 140 are then transmitted to the computer 1000 for processing into data and for storage of that data, as described below. In some embodiments, some amount of, or all of, the processing of the signals into data will occur prior to the storage of the data, while in other embodiments, the analog signals will merely be converted into digital raw data and will then be stored directly, without significant further processing. The signal from the detector 140 is in the form of electrical pulses that have amplitudes that represent the energies of the detected gamma rays. The amplitude of each pulse is communicated from the detector 140 to the computer 1000. The spectral data are accumulated in the computer 1000 and can be presented as a histogram of the number of gamma rays of each energy that have been detected during an accumulation period or interval.

After spectral data are either stored or processed, or both, the computer 1000 can provide a particular type of output via the input/output module 1050/1060 to provide feedback or results to users. The output delivered depends on the application for which the system 100 is used and is described later, but can range from mere graphical or alphanumeric display to a network-linked system for operating and monitoring processes, for testing or for surveying the elemental composition of the ground in an area or for any other relevant purpose.

A. Analyzer

Figure 2:
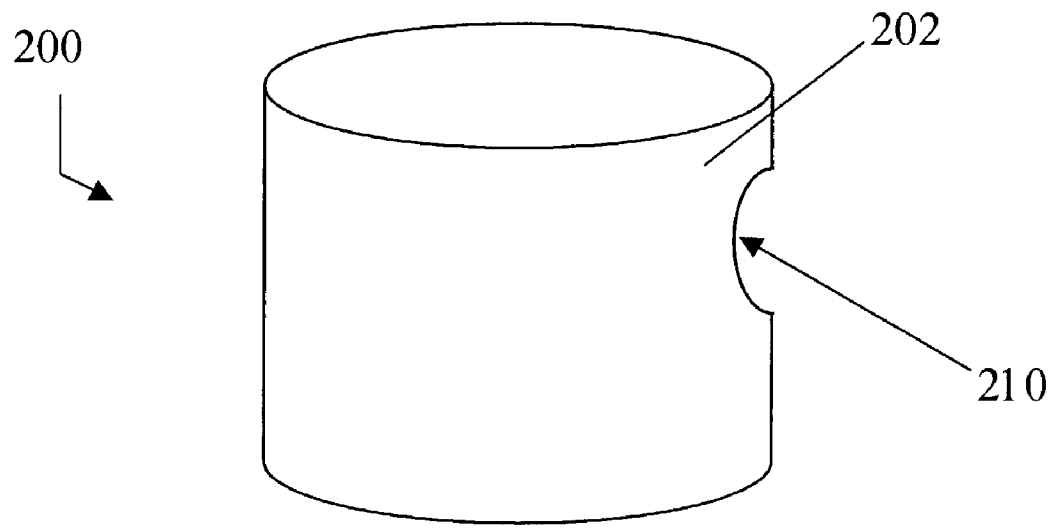
FIG. 2 is a perspective view of inner and outer forms that can be used to form a housing structure for one embodiment of a materials analyzer.
Figure 2:
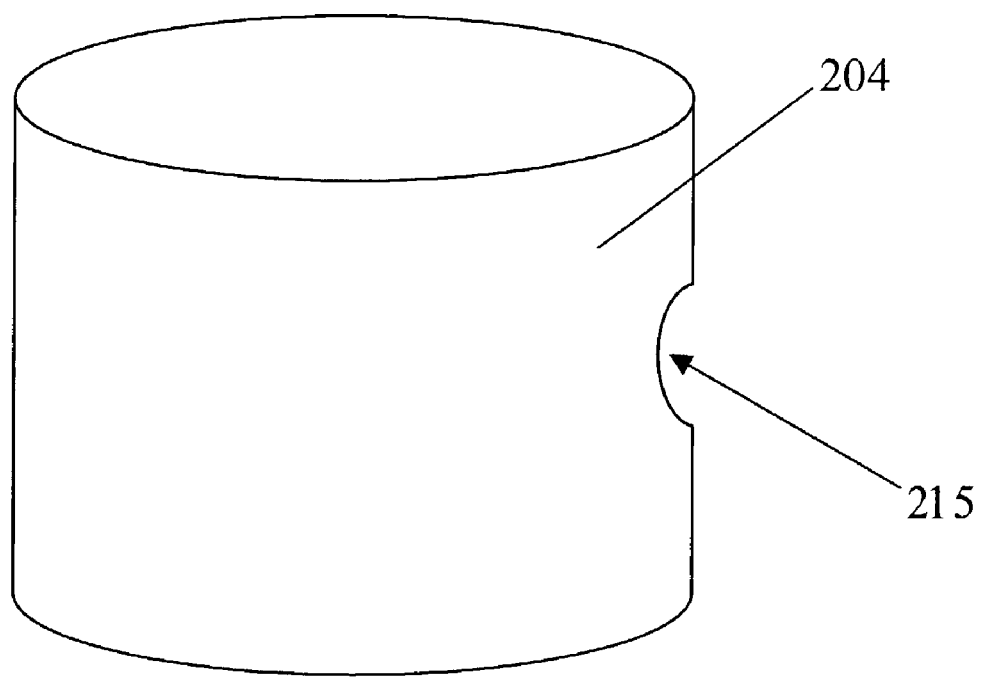

Referring to FIG. 2, an exploded view of inside and outside containers 202, 204, respectively, of an analyzer housing 200 are illustrated. In certain embodiments, the outer container 204 of a material analyzer housing 200 is formed by an outer drum, while a smaller, inner drum forms the inner container 202 of the housing 200, although any shaped or sized inner and outer containers 202, 204 can be used and the shapes of the inner container 202 and outer container 204 can be different. By placing the inner container 202 inside the outer container 204, a space (not shown) is formed between the two containers 202, 204, and the containers 202, 204 together with the space between them form an analyzer housing 200. This analyzer housing 200 is unique compared to the analyzer housings constructed of blocks of shielding material that are currently available. In some embodiments, a round housing is used and the shape of these embodiments reduces the size and weight of the housing 200 over past analyzers that included excess and superfluous materials in their designs. For reduction in the cost of manufacturing such housings 200, the outer container 204 and the inner container 202 can be standard sized barrels that are commonly made for liquid and solid storage or salvage. For instance the outside container 204 can be a barrel made of metal such as steel, and can be, for example, about 30 inches in diameter and 30 inches high, such as is defined by a short version of a standard 110-gallon capacity steel salvage drum. The inner container 202 can be a 55-gallon drum made of a polyethylene or any other material. The containers 202, 204 can be commercially available containers of any type and size to reduce manufacturing costs for the housing 200. The housing 200 can be modified with a number of openings 210, 215 to accommodate detectors, sources, and sample material insertion or flow. Additional housing portions (not shown) may also be attached to the inside and outside containers 202, 204 as integral pieces of the housing 200, such as a detector penetration housing or a lid to close the top.

B. Portable, Static-Sample Analyzer

Figure 3:
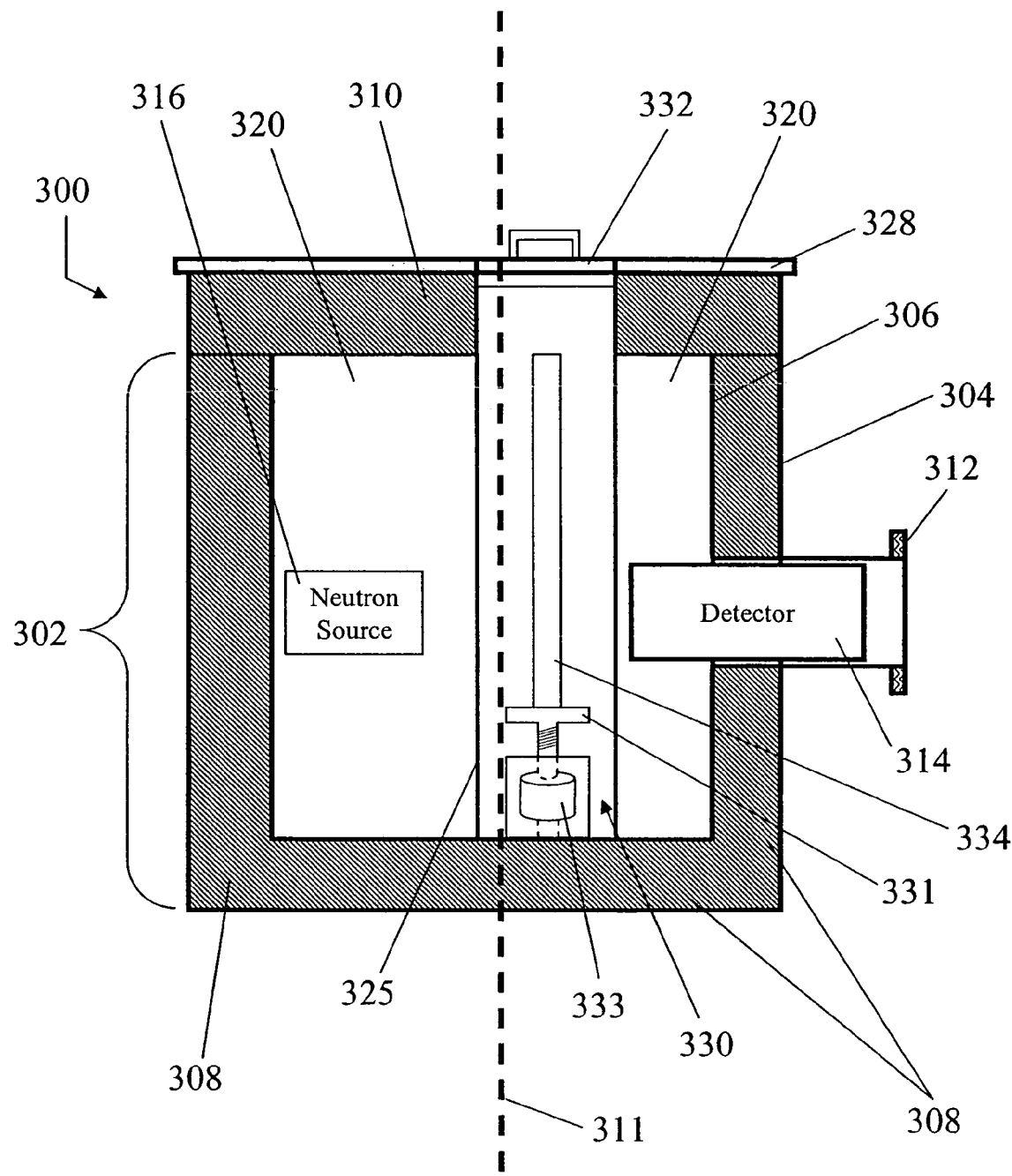
FIG. 3 is a cross-sectional view of one embodiment of a materials analyzer taken along line 3—3 of FIG. 1.
Figure 3A:
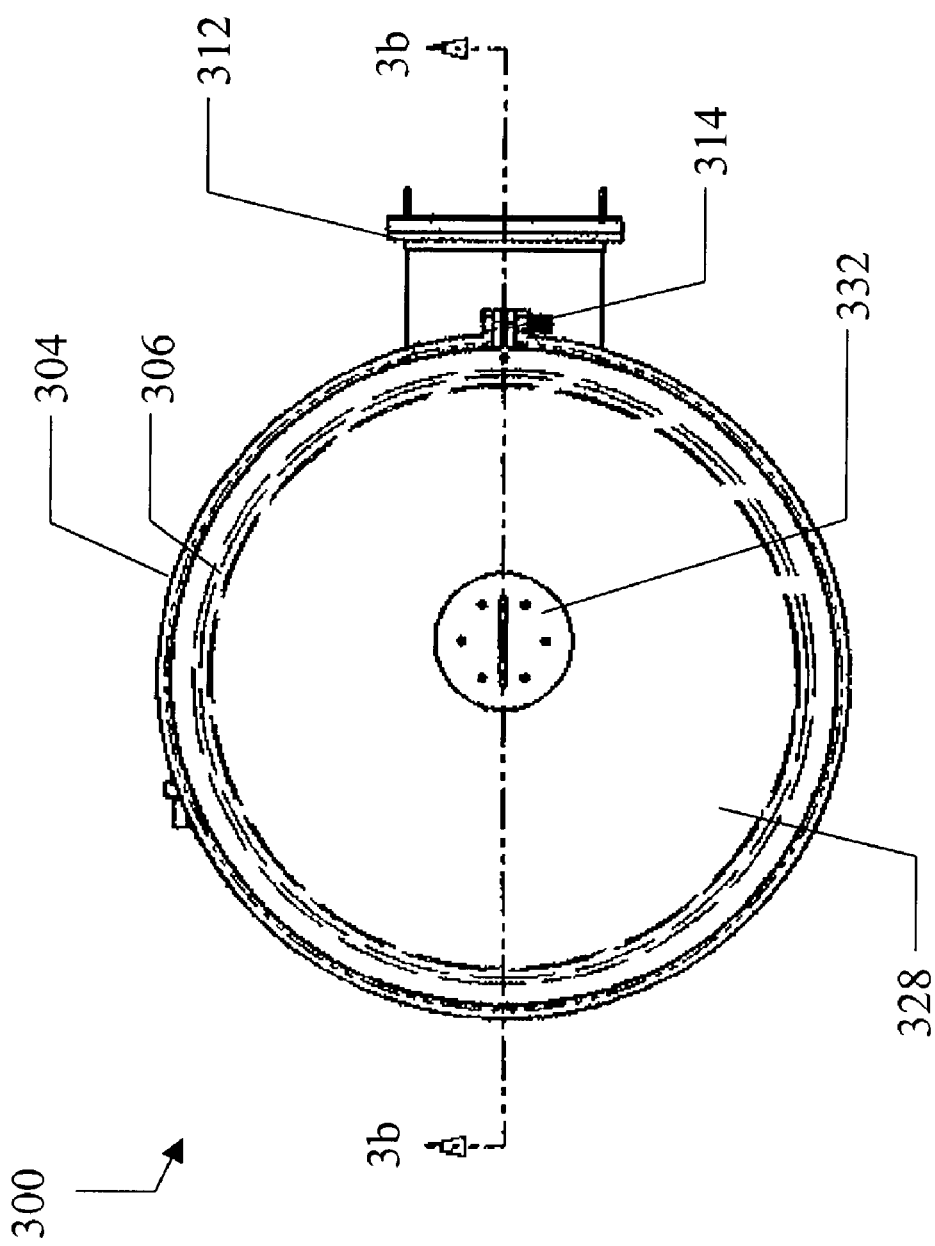
FIG. 3a is a top view of one embodiment of a static sample analyzer.
Figure 3B:
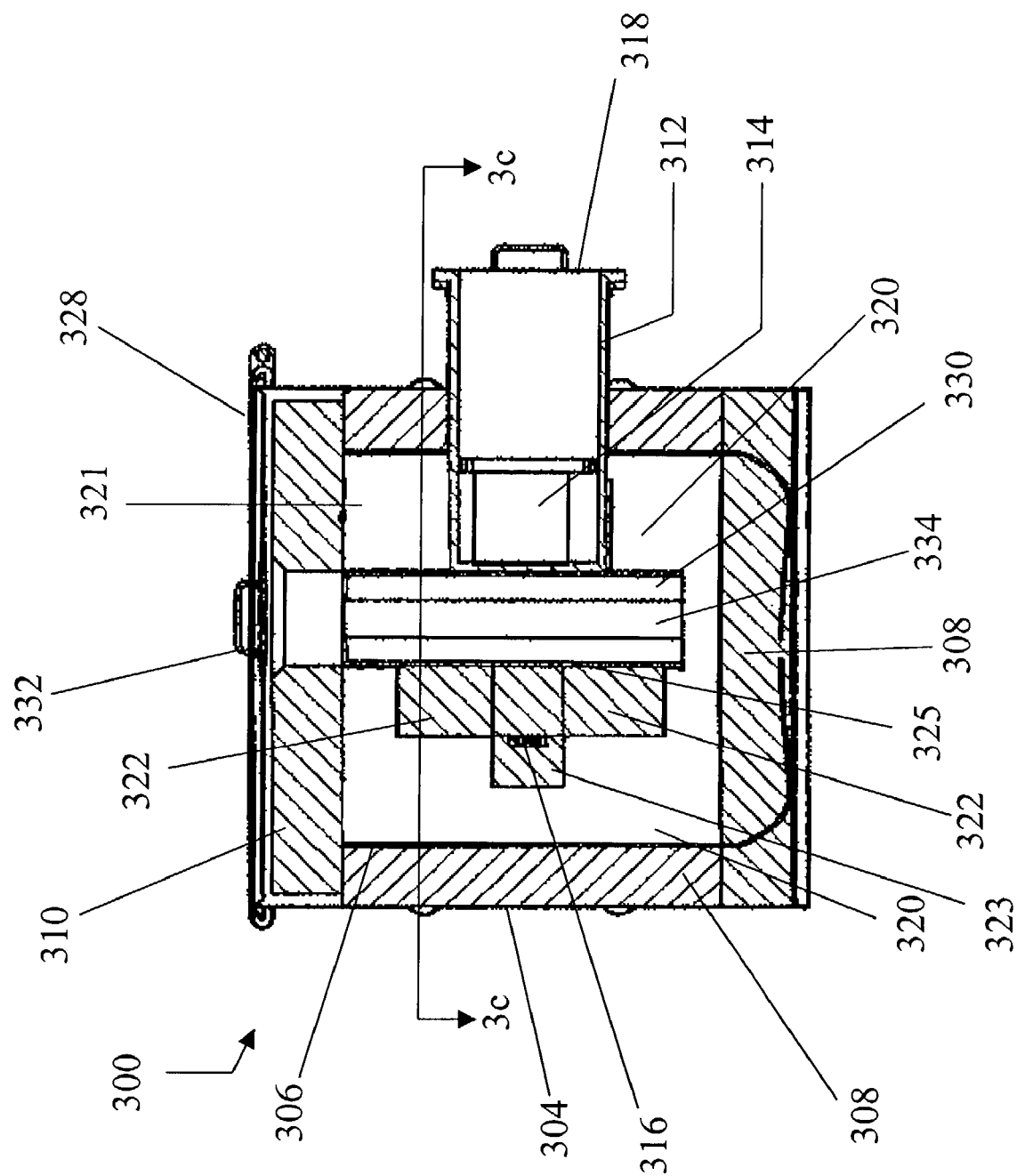
Figure 3C:
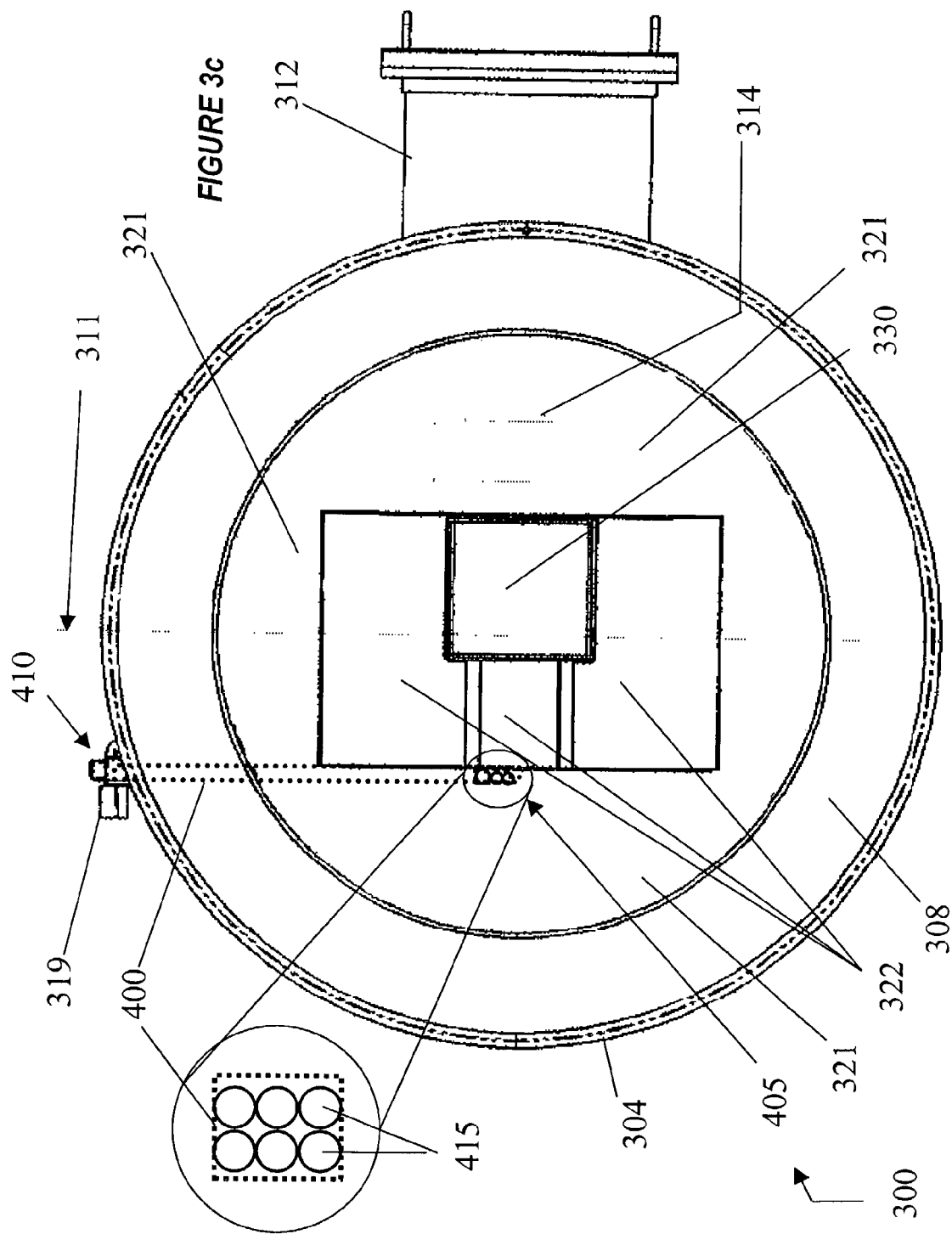
FIG. 3c is a cross-sectional view of one embodiment of a static sample analyzer taken along line 3c—3c of FIG. 3b.
Figure 4:
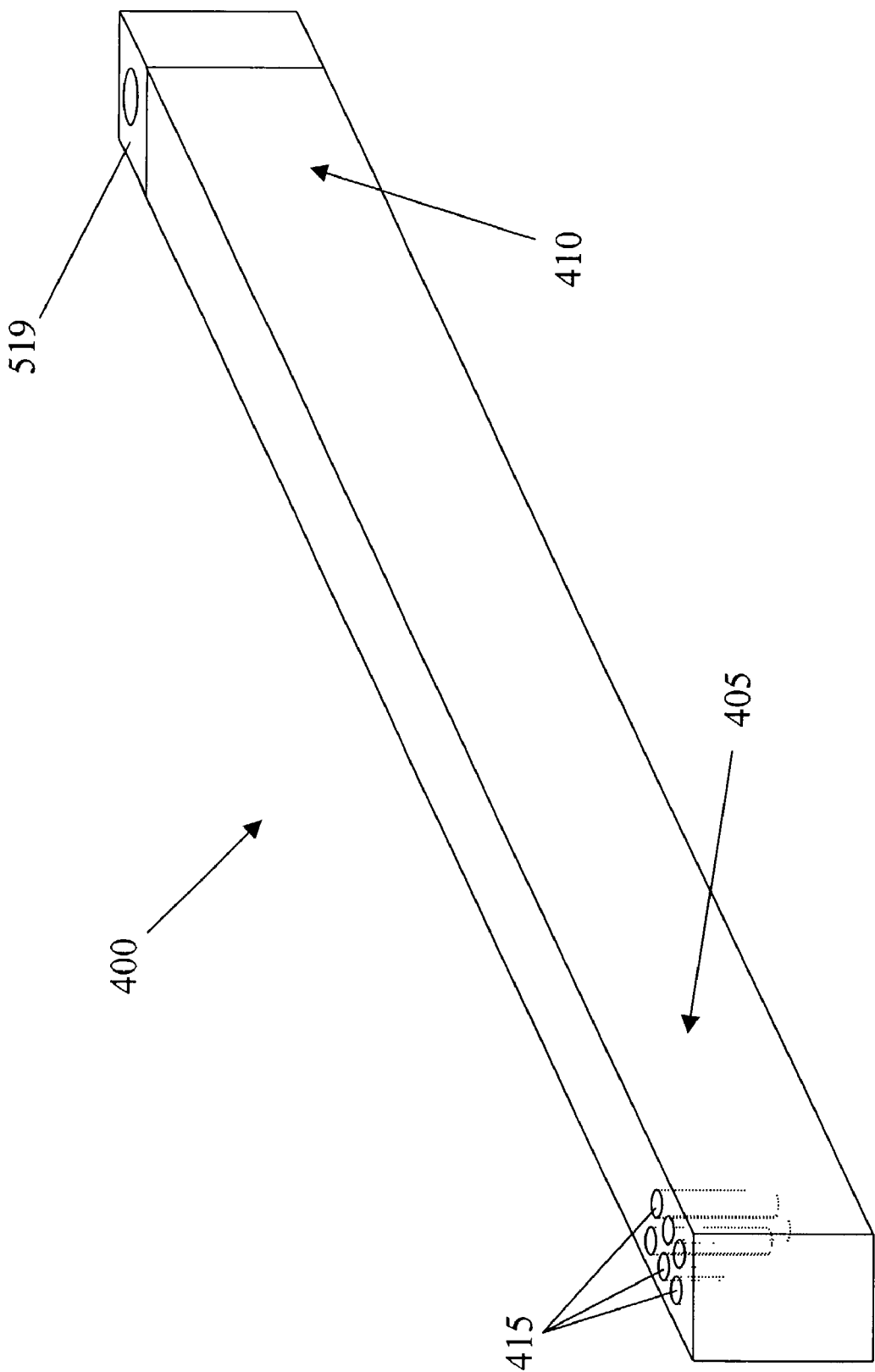
FIG. 4 is a perspective view of one embodiment of a source holder use with the analyzer of FIG. 3.

One embodiment of a materials analyzer is a portable, static-sample analyzer 300 as is illustrated in FIG. 3, employing an embodiment of the housing 200 illustrated in FIG. 2. In a static sample analyzer 300, the material in the analyzer does not flow through the analyzer, but rather is a closed system of material to be analyzed. Used in this manner, the term static is not intended to imply that the material does not move, as will be described later, rather, it means there is no mass exchange into or out of the sample. Further features of such an analyzer are illustrated in FIGS. 3a, 3b, and 3c. A housing 302 of the analyzer 300 comprises, in some embodiments, an outer container 304 and an inner container 306, wherein the outer container 304 has a larger volume than the inner container 306. For certain embodiments, the outer container 304 has the diameter and construction of a 110-gallon salvage drum that is standard in the drum-manufacturing industry, and the inner container 306 has a volume of a smaller drum that is also standard in the drum-manufacturing industry. In some embodiments, the outer container 304 can be a standard commercially available 110-gallon steel drum and the inner container 306 can be a commercially available 55-gallon polyethylene drum, thereby reducing manufacturing costs of the housing 302. Although any standard containers can be used, and the inner container 306 and the outer container 304 can be different shapes and different sizes.

A gap between the outer container 304 and the inner container 306 is filled with a shielding material 308, and the bottom of the inner container 306 can also be filled with the shielding material 308, so as to provide additional shielding and a flat surface in the bottom of the analyzer housing 302. In some embodiments, an amount of shielding material 308 will be placed in the outer container 304 and then the inner container 306 will be pressed down into the outer container 304 thereby containing all of the shielding material 308 between the two containers 304, 306. Some embodiments use a pourable shielding material 308 that can fill the void space between the inner and outer containers 306, 304 and can be formed to define the bottom shielding of the housing 302. One such material that can be used is a composite, including water-extended polyester available from Ashland Specialty Chemical Company in Columbus, Ohio, although any other material that can exist in fluid-like or slurry form and then solidify and remain solid can be used. These other materials can include, for example, any cement, epoxy, resin, or other such material. Many embodiments will mix, either discretely or homogeneously, a neutron-absorbing ingredient (not separately identified) into the pourable shielding, thereby increasing the shielding value, or capability, of the shielding material 306. The neutron-absorbing ingredient can be any material that absorbs neutrons, with higher values of cross section of absorption of neutrons being more effective, such as for example boron, cadmium, gadolinium, samarium, dysprosium, europium, or actinium, or any other neutron-absorbing material. Some embodiments will use neutron absorbing materials having a microscopic cross section for absorption of neutrons of 10 barns (1 barn=$10^{-24}$ cm$^2$) or greater, while some embodiments will utilize materials having such a microscopic cross section of 100 barns or greater. Examples of materials include, for example and not by way of limitation, boron, cadmium, indium, samarium, europium, gadolinium, dysprosium, thulium, lutetium, hafnium, iridium, mercury, actinium, protactinium, neptunium and plutonium. A mixture containing hydrocarbons and 15 percent boron will provide good neutron shielding. Alternatively, an appropriate shape can be cut out of any number of commonly available blocks of the desired thickness of borated polyethylene, or any other suitable shielding material to form the bottom of the housing 302 illustrated in FIG. 3. Additionally, a number of rings (not shown) that have been cut out of a similar or the same material can be stacked successively upon the bottom and then one another to form the rest of the housing 302 illustrated.

A disc shaped shielding top 310 can be formed from material that is the same as the shielding material 308, or can be of different material to produce different shielding effects, depending on the application. Although a top 310 is described herein, the usage of that term is only conventional for the illustrated embodiment and the analyzer can be on its side or at any angle, and the top 310 would be adjusted accordingly to enclose the internal portions of the analyzer 300. This shielding top 310 can be made using a form and pouring a top 310, with a pourable material similar to that described for the shielding material 308 that hardens to form the top 310. The shielding top 310 is designed to have a circumference that fits within the wall of the outer container 304 and so that the top 310 rests on top of the inner container 306 and shielding material 308. Additionally, a lid 328 can be permanently fastened to the rest of the structure of the analyzer 300 or it can be temporarily secured so as to permit access to the inner compartments of the analyzer for maintenance and upkeep, such as with a band clamp or some other removable fastening system. In many embodiments, the housing 302 is centered about a longitudinal axis 311, which also forms an axis about which the outer container 304, the inner container 306, the shielding material 308 and the shielding top 310 are also centered. Thus, as a material sample 334 and a neutron source 316 are inserted in the analyzer, they are shielded in both vertical and horizontal directions. The amount of shielding material 308 used in the analyzer 300 can be modified to allow external radiation fields to approach the levels allowed by government regulations. The reduction in shielding material and the radiation emission levels can be carefully controlled to allow for reduced size and weight of the analyzer 300 while maintaining safe levels of radiation emission outside the analyzer 300.

As illustrated in FIGS. 3, 3a, 3b and 3c, the housing 302 can be modified to include an integral detector housing 312 to accommodate installation of a detector 314. In many embodiments, the detector housing 312 is a tubular fitting that passes through the housing 302 generally perpendicular to, and extending radially inward towards, the longitudinal axis 311 of the analyzer 300. However, any orientation that allows the detector to receive gamma rays from the sample can be successful. The detector housing 312 can include shielding around and in front of and/or behind the detector 314. The detector housing 312 does not extend all the way to the longitudinal axis 311 of the analyzer 300 in several embodiments. A detector cover 318 secures the detector 314 into its position while allowing conductors (not shown) to pass through the detector housing 312 to the detector 314 to provide power to the detector 314 and to receive detected spectral data from the detector 314 for analysis.

Referring to FIGS. 3, 3a, 3b, 3c and 4, the housing 302 can also be modified in some embodiments to provide an insertion path for a neutron source 316 and a source holder 400. The insertion path can be a horizontal, vertical, or any other angled slot extending inward from the outer container 302 such that the neutron source 316 can be slid into the analyzer 300 for activation of the sample of bulk material to be analyzed. The source holder 400 is a generally elongated member having a first end 405 for holding one or more neutron sources and a second end 410 that extends through the insertion path to the outside of the analyzer housing 302. In several embodiments, the second end 410 of the source holder 400 and the associated part of the housing 302 will have a locking feature 319 to secure the source 316 in its place. The locking feature 319 may be a ring and a lock, an electronic locking device, a keyed fastener or any other type of locking device. In the embodiment illustrated, the source holder 400 has a rectangular cross-section, however, this is only for illustrative purposes and any cross sectional shape can be used. The first end 405 of the source holder 400 has one or more holes 415 for receiving one or more radioactive sources 316. In one embodiment, one source 316 is initially placed in one of the holes 415 in the first end 405 of the source holder 400. When the radiation emitted from the source 316 has decayed to a certain level the source holder 400 is unlocked and a second source 316 is placed into a hole 415 in the source holder 400. Additional sources 316 can be added in this manner repeatedly, replenishing the source 316. The predetermined level at which the source 316 is replenished can be any level the operator chooses, and in some embodiments is when the source 316 has decayed to half of its source strength. In some embodiments, the material of the source holder 400 can moderate and shield source neutrons and shield the gamma rays emitted by the source 316, thereby lowering the amount of gamma radiation exiting from the housing 302.

In several embodiments, the source 316 is positioned angularly opposite from the detector 314 with respect to the longitudinal axis 311 of the analyzer 300, however the source 316 can be placed in any position with respect to the detector 314 that provides an appropriate neutron flux field in the sample volume 330. In some embodiments, multiple sources may be used to shape the neutron flux interacting with the materials being sampled. Moderating/reflecting/shielding material 320 can be inserted and arranged in the inner structure of the analyzer, generally within the inner container 306. The moderating/reflecting/shielding materials 320 serve several functions and can be made of a combination of materials that individually fulfill one of these functions or can be made of a combination of materials that fulfill more than one of these functions. For example, the moderating/reflecting/shielding materials 320 shield neutron-source gamma rays and moderate the energy of the neutrons in the analyzer to increase absorption of the neutrons by the atoms in the sample 334. The moderating/reflecting/shielding materials 320 also reduce unwanted radiation in the detector and act to reflect neutrons back toward the sample 334, thereby lowering the number of neutrons that escape the analyzer 300. By fulfilling these functions, the moderating/reflecting/shielding materials 320 control the thermal neutron population in the analyzer 300, and thereby enhance neutron absorption in the sample 334 while aiding neutron and gamma radiation shielding.

The moderating/reflecting/shielding materials 320 can include materials such as polyethylene, carbon, bismuth, lead, and boron, however any other materials that can fulfill one or more of the indicated functions can be used in combination with other materials. Some embodiments will also surround the source 316 with gamma ray attenuating material and arrange the moderating/reflecting/shielding materials 320 for focusing the neutrons into the sample 334 of material to be analyzed. Materials used for reflecting will generally have a high scattering cross-section and a relatively low cross-section of absorption of neutrons. Water can be used as a reflector, but any other material having the desired properties can be used as well, such as for example, polyethylene, and iron. Referring to FIGS. 3b and 3c, an embodiment is illustrated wherein the moderating/reflecting/shielding material 320 of FIG. 3, is further illustrated as polyethylene 321, graphite 322 and lead 323. Although, any combination of these or other materials described herein can be used for the moderating/reflecting/shielding material 320 of the analyzer 300

A sample volume 330, which can be a simple hole (not separately identified) bored into the analyzer 300, can be formed in the shielding top 310 and down through the moderating/reflecting/shielding material 320 to accommodate a material sample holder 325. The sample volume 330 does not have to be in the center of the analyzer 300, and in several embodiments, as illustrated by FIG. 3, is offset from the longitudinal axis 311 of the analyzer 300. In many embodiments, the sample volume 330 will be in a direct path from the source 316 to the detector 314 to simplify analyzer 300 construction. A cover 328 can be placed on top of the outer container 304 and the shielding top 310 to seal the contents of the analyzer 300, wherein the cover 328 also has a hole (not separately identified) in it to accommodate insertion of the material sample holder 325 and a dust cover 332 for covering the hole.

Still referring to FIGS. 3, 3a, 3b and 3c, the sample holder 325 can be cylindrical in shape and hold a cylindrical volume of a material sample 334 having a generally circular cross section, although other embodiments may have a curved or rectangular shaped cross section. The sample holder 325 is inserted into the analyzer 300 from above the analyzer 300 and is extended into the sample volume 330 passing the detector 314. In some embodiments, the sample holder 325 is made of a material that contributes little signal to the gamma-ray spectrum. Carbon and oxygen both have low probabilities of neutron interaction, or cross-sections for absorption, and hydrogen gives off only one energy gamma ray. Therefore, some embodiments use hydrocarbons for the structure of the sample volume. For example, ABS pipe is used in some embodiments, although any material can be used with the corresponding analysis to obtain appropriate results, while other embodiments use a reactor-grade zirconium. Reactor-grade zirconium can be described as zirconium having a very low level of impurities, such as for example and not limitation, less than 1% impurities, or alternatively, less than 1 ppm (part per million) impurities, wherein the impurities may include for instance hafnium. Furthermore, the sample holder 325 can be made from a standard pipe capped on the bottom and open or covered on the top, for a simple and effective way of maintaining consistent inner and outer diameters. For example, the sample holder 325 may be a 4-inch, ABS pipe that is 15 to 25 inches long where the analyzer 300 is about 30 inches in diameter and about 30 inches high. The pipe can be longer than the vertical sensitive area of the detector 314 and a have fixed cross-sectional area, so as to ensure that the solid angle from the sample material 334 intercepted by the detector 314 is constant if the sample holder 325 is full.

In some embodiments, as illustrated in FIG. 3, the detector 314 and the neutron source 316 are positioned on opposite sides of the sample 334, however such an orientation is not required and any other orientation or multiple sources 316 can be used, as will be described below with respect to FIG. 6. Though the neutron source can be on a single side of the sample 334, the neutrons are moderated and reflected by the moderating/reflecting/shielding materials 320 into the sample 334 from all directions and the gamma rays are emitted in all directions from the sample 334. Therefore, it is not necessary for the detector 314 and the source 316 to be on opposite sides of the sample 334. In some embodiments, neutrons from the source 316 are focused into the sample 334 and the detector 314 is shielded from radiation emitted directly from the source 316. For example, the sample 334 to be tested may be in a cylindrical form and inserted vertically into the analyzer 300, and the neutron source 316 may be located in an angular direction, with respect to the longitudinal axis 311 of the cylindrical housing 302, toward the detector 314. However, certain embodiments provide a configuration of moderating/reflecting/shielding materials 320 that shield the detector 314 from gamma rays emitted directly from the neutron source 316, thereby allowing for any position of the source 316 with respect to the detector 314. Additionally, in such embodiments, the radiation from the source 316 can be removed in data analysis to compensate for the different positioning with a knowledge of the gamma ray emission characteristics of the sample 334. In one embodiment, a load cell (not shown) can be used to support the sample holder 325 to provide a measurement of the mass of the material sample 334. Such a measurement allows a user to compensate for differences in material density for certain material samples 334. For many materials that are analyzed, density measurement is not necessary as differences in density can be compensated for in the data analysis algorithm described later, however, some materials may require a density measurement for proper analysis if the mass of the material sample 334 cannot be determined from the spectral data.

Because many types of materials are not homogeneous in their compositional makeup or their physical structure along the volume of the material sample 334, the non-homogeneity of samples can result in different analysis results if the material sample 334 is removed and reloaded into the sample holder 325. This is due to a variance in the sensitivity of the detector 314 to gamma rays emitted from different locations in the material sample 334, especially in the vertical direction, along the longitudinal axis 311. This effect is minimized by rotating the sample and moving it in a vertical direction during data collection to ensure uniform sensitivity in each position within the sample volume 330, which extends beyond the measurement zone of the detector. An elevator 331, such as a piston, can be used, for example, to move the material sample 334 in a vertical direction while a rotator 333, such as a motor, can be used to rotate the material sample 334. The elevator 331 can be any device capable of providing vertical displacement of the material sample 334, and in certain embodiments will provide incremental or continuous vertical location information for use in the data analysis process. Similarly, the rotator can be any device capable of providing angular rotation of the material sample 334, while certain embodiments will provide incremental or continuous angular position signals for use in the data analysis process.

C. Clinker Analyzer

Figure 5:
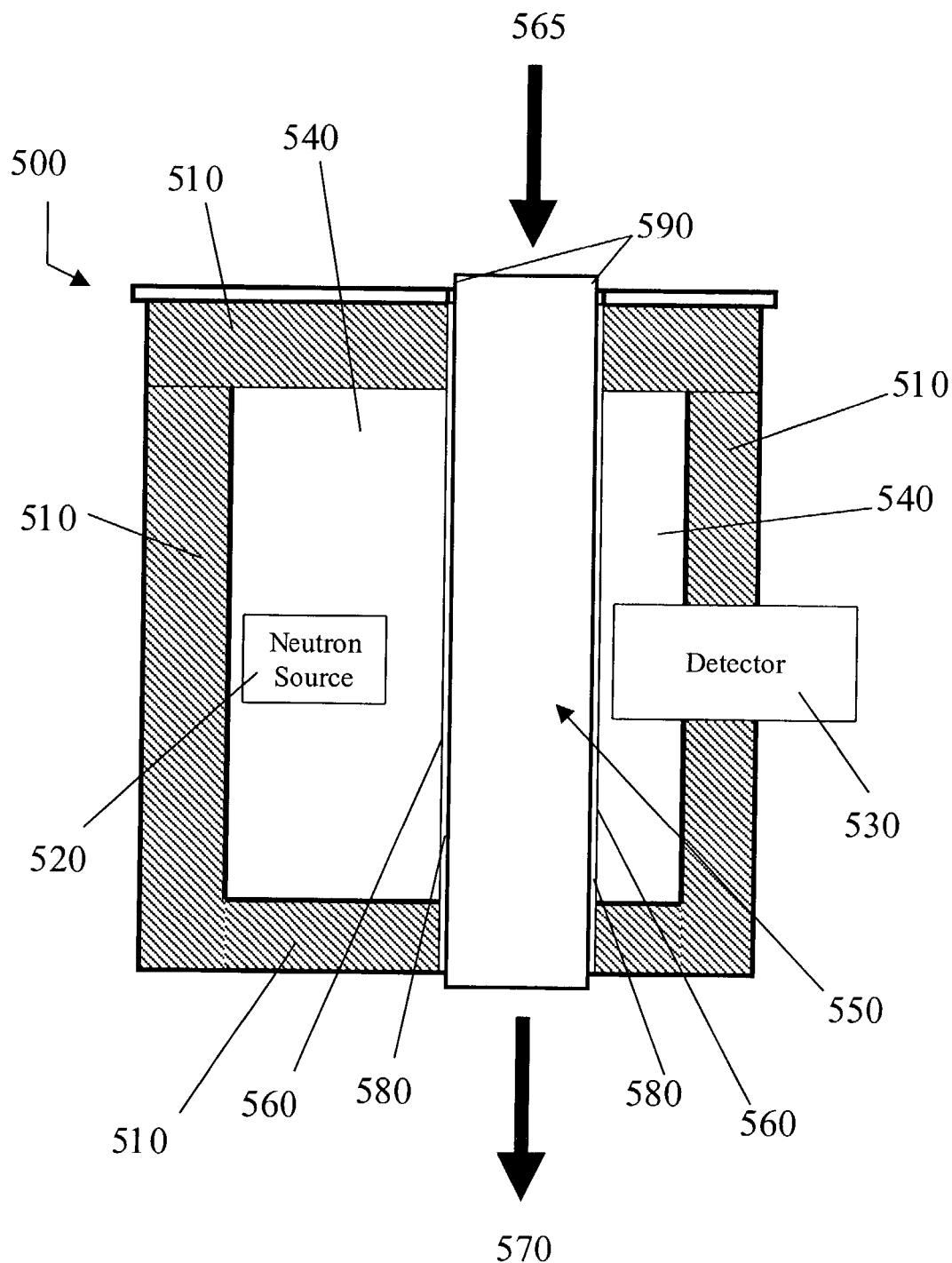
FIG. 5 is a cross-sectional view of one embodiment of an analyzer taken along line 3—3 of FIG. 1 using an open sample volume for a flow of sample material through the analyzer.

One embodiment of a PGNAA analyzer is an on-line sample flow-through analyzer 500 illustrated in FIG. 5. Many different applications can use such an analyzer and many such applications will be characterized by a flow of solid materials of many varieties through the analyzer 500. One embodiment of an on-line sample flow-through application is cement clinker. Clinker, as used herein with reference to FIG. 5, can generally be described as any amount of bulk material, including certain solid materials formed in a kiln in a cement plant. Cement manufacturers have a need for on-line, or real time, analysis of the compositional makeup of the cement clinker in order to more effectively control their processes. As illustrated in FIG. 5, an analyzer 500 for cement clinker can have a housing 510, as described above with reference to the housing 302, 310 of FIG. 3, for housing a neutron radiation source 520 and a gamma ray detector 530. In addition, the analyzer 500 can include moderating/reflecting/shielding materials 540 to fulfill the functions described above. In the cement clinker analyzer 500, on-line analysis is allowed by using an open sample volume 550 having an inlet 565 area for material to enter, or flow into, the sample volume 550 and an outlet 570 area allowing the material to leave the analyzer 500. In embodiments such as this, the cement clinker enters the sample volume 550 at the inlet 565 and flows past the neutron source 520 where it is irradiated and emits capture gamma rays that are detected by the detector 530, and then exits the analyzer from the outlet 570. In this manner a steady flow of cement clinker past the neutron source 520 and detector 530 provides a steady supply of data representative of the material composition of the cement clinker flowing through the analyzer for that period. By ensuring the sample volume 550 is significantly longer than the measurement field of the detector 530, the sample volume can be treated as an endless line of material, thereby eliminating the need for determining the end effects of the material in the sample volume 550.

Cement clinker is very abrasive, however, and, at locations where it can be sampled, may range in temperature from about 60 degrees Celsius to about 80 degrees Celsius, reaching temperatures as high as 1000 degrees Celsius during transient upset conditions. These conditions, including the abrasive quality and the high temperature, can damage the surface 560 of the sample volume 550 as the cement clinker passes through the analyzer 500. To counter such destructive effects, the analyzer 500 can be modified such that the sample volume surface 560 is lined with a protective coating 580. In some embodiments, this protective coating 580 will be a thin metal skin, but any material can also be used to protect the surface 560, such as porous carbon or other such material, an air gap, or any combination of the preceding. In some embodiments, the sample volume 550 encircles a pipe 590, through which the clinker flows, providing additional protection from the destructive properties of the clinker. The pipe 590 may be steel, zirconium, zircalloy, inconel, cast iron, monel, k-monel, stainless steel or any other protective material, or could be whatever piping a cement manufacturer is currently using to convey cement clinker, but certain embodiments will utilize a material contributing little to the detected spectral data. In some embodiments, the pipe in the sample volume 550 can be positioned at some predefined angle, and is not limited to the vertical position shown in FIG. 4.

The 1000-degree Celsius temperature of the clinker can harm some of the materials and components inside the analyzer. Therefore, porous carbon (also at 580), or other insulating material, can be used next to the steel skin in the measurement zone to insulate the other materials from the 1000-degree temperature of the clinker material. In areas where it is practical, an air gap can be used for this purpose. A temperature sensor (not shown) can be used to monitor the temperature of the clinker. If upset conditions occur, the clinker flow can be stopped and the clinker pipe 590 emptied so as to limit the duration of 1000-degree Celsius temperature exposure of the analyzer 500. This procedure can be employed to protect the analyzer 500. Also, to keep the normal temperature of the analyzer 500 in a moderate range and to extend the life of the analyzer 500, air can be blown along the length of the clinker pipe 590 that passes through the analyzer 500.

Therefore, one embodiment of an analyzer 500 for analyzing the compositional materials of cement clinker is illustrated and described wherein a steady flow of a substance such as cement clinker can be analyzed in real-time to determine the compositional makeup of the substance as it moves through its processing steps. The cement clinker enters the analyzer sample volume 550 through an inlet 565 and exits through an outlet 570 after passing through the measurement zone near a neutron source 520 and a gamma ray detector 530 that provides the signal for analyzing the cement clinker. Additionally, due to the improved construction techniques described above, the analyzer 500 takes up much less space in the processing plant than the prior art systems, occupying as little as about twelve cubic feet. Space in a cement plant where real-time clinker measurement may be made is limited. Prior art PGNAA instruments have not been designed to measure cement clinker, and many plants could not accommodate the typical size of such instruments, that size typically being 870 or so cubic feet. The relatively small size of this cement clinker analyzer 500 allows cement producers to install it in a convenient location without significantly modifying their plant. Prior art analyzers are much larger and, therefore, much more costly and inconvenient.

D. Slurry Analyzer

Still referring to FIG. 5, a coal-slurry analyzer can be produced that is similar to the clinker analyzer 500. The same analyzer 500, with modifications to accommodate the needs of the particular slurry, can be used with many other types of slurry, such as cement slurry or phosphate slurry. The physical structure of the coal slurry to be measured has a different geometry and consistency from cement clinker. The temperature of the coal slurry is typically 5 degrees Celsius to 30 degrees Celsius and a representative sample stream of a few gallons per minute may be available for real-time analysis. Therefore, the structural materials for the sample volume 550 can also differ from those of the clinker analyzer 500 described above.

For coal-slurry analysis, it is advantageous to have sufficient slurry pass through the analyzer sample volume 550 such that a signal can be obtained from the coal that can be distinguished above the signal from the analyzer structure 510, 540, 560, 580, 590. By doing this, the analyzer 500 provides a data spectrum that is more representative of the material being measured. However, a very large sample volume 550 can make uniform sensitivity of the measurement over the entire sample volume 550 more difficult. For example, an element in one location in the sample volume 550 would contribute a different amount of signal than the same element in a different location in the sample volume 550. This contrast is due to a difference in the solid angle intercepted by the detector 530 for a given distance from an emitting nucleus, as well as the differences in attenuation of the signal by materials between the emitting nucleus in the sample volume and the detector 530. Simply put, the farther the detector 530 is from the emitting nucleus, the less chance there is that a gamma ray emitted from the nucleus will hit the detector 530, both because it becomes a smaller target and because there is more material along the gamma ray's path with which it might interact before reaching the detector 530.

Non-uniform sensitivity across the sample volume 550 can be compensated for, however, by tailoring the neutron flux, the average number of neutrons passing a given area during a particular period of time, to suit the geometry of the sample volume 550. Alternatively, the non-uniform sensitivity across the sample volume 550 can be minimized by reducing the thickness of the sample volume 550 in front of the detector 530 and making the width of the sample volume 550 in front of the detector 530 larger. By changing the configuration of the sample volume 550, the differences in the solid angle intercepted by the detector 530 for any point in a plane orthogonal to the direction of flow of the material being measured are small, and the differences in attenuation of the signal by material between any emitting particle and the detector 530 are also small. Differences in the solid angle intercepted and attenuation in the direction of flow of the material being measured are self-compensating because the material flows continuously through the analyzer 500. In one embodiment for example, a cross-sectional area of about three inches thick by ten inches wide, where laminar flow characteristics are established along a length of over 20 inches along the flow channel defined by the sample volume 550, can be used for a six inch diameter detector 530. In such an embodiment, the channel, or sample volume 550, formed in the analyzer 500 is substantially rectangular, while other embodiments may be circular or some other curved shape. The cross-sectional sample area adapted to the size of the detector allows improved performance of embodiments of the present analyzer 500.

E. Mechanical-Sample Analyzer

Many current measuring systems are based on measuring a representative sample of the materials being processed at various stages in the process rather than continuously measuring all of the material being processed. Many mechanical sampling systems for obtaining such representative samples take the form of knife-edge samplers or sweep-arm samplers. The knife-edge sampler passes a collection container underneath the exit end of a process conveyor containing the material of interest and the sweep-arm sampler uses a sweeping, broom-like device to sweep a sample off of a moving process conveyor containing the material of interest. Each system is set to have a sampling frequency that will ensure that a total sample collected over some period of time will be representative, on average, of the elemental composition of the material that has passed by on the process conveyor. In addition, many of these systems have crushers of some type to reduce the topsize of the material in order to facilitate laboratory analysis of the material. These systems also employ some means of consistently reducing the total mass of the sample while retaining the level of how well the samples represent the material on the process belt. Many systems deliver the final sample, which may be a secondary or tertiary sample, into a container that more or less resembles a 5-gallon milk can. Many industrial-material processors, such as coal mines, utilize a mechanical sampling system of some kind and the systems are all located at the one or more points in the process where a sample will be the most meaningful in terms of the customer's needs. These sampling systems can be referred to as sampling mechanisms, which are in-line sampling systems for obtaining representative samples of materials for sending to a laboratory for analysis.

These mechanical sampling systems utilize pipes and chutes to move the various stages of samples, such as primary cuts, secondary, tertiary, and final samples, from the original process belt to the crusher, back to the process and to the final sample container. These pipes and chutes lend themselves to the application of embodiments of the analyzer described herein with a minimum of construction costs. Embodiments of the on-line analyzer described herein can be used in such sampling mechanisms to provided real time analysis results of the samples, which is an improvement of systems experiencing a much more extensive delay associated with laboratory analyses. Embodiments of the on-line nuclear elemental analyzer described herein are the first ones ever designed with a small enough footprint to make this approach an option that can be seriously considered by coal mines, coal prep plants, coal burning utilities, cement plants, mineral processing plants, or any other industry that can benefit from timely material analyses.

F. Conveyor Belt Analyzer

Figure 6:
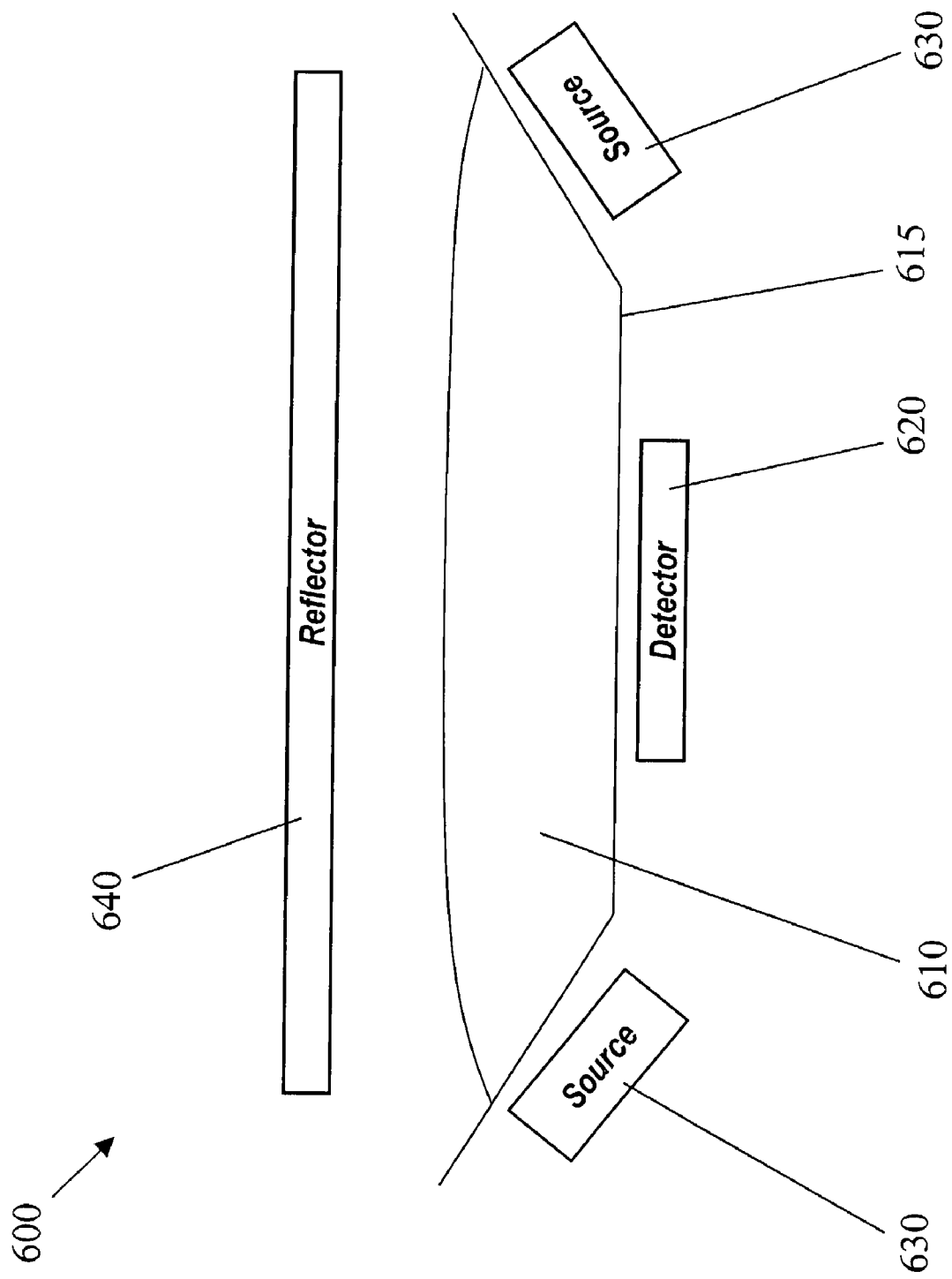
FIG. 6 is a cross-sectional view of one embodiment of a conveyor system materials analyzer taken along a line perpendicular to the flowpath of the conveyor and midway through the analyzer.

FIG. 6 is a schematic representation of one embodiment of an analyzer 600, capable of analyzing bulk material 610 being transported on a conveyor belt 615. The components of the embodiment illustrated in FIG. 6 have similar features and functions as their counterparts described above with respect to previous figures. This analyzer 600 is installed along the path of a conveyor system (not shown) in a material transportation system of any type of application where it is desirable to determine the presence of certain elements in bulk material 610 that is transported along such a system. Examples of applications that can use such an analyzer 600 include cement materials processing, coal mining and processing, other quarry and mining operations and any other such application. While a conveyor belt is illustrated in FIG. 6, any conveying system can be used that moves the material to be sampled past the analyzer 600. For example, a conveying tube may be used to convey materials, wherein such a conveying tube can be a pipe or any other curved or rectangular passage for the conveying of materials.

The analyzer 600 illustrated in FIG. 6 has a detector 620 for detecting gamma rays from the sample material 610 and one or more neutron sources 630. For several embodiments, two sources 630 are used along with a reflector 640 to redirect escaping neutrons back into the sample material 610, although more or less sources 630 can be used. The reflector 640, as described above, is a material capable of redirecting the neutrons emitted by the sources 630, such as polyethylene, water, steel or any other material. In some embodiments, the sources 630 are located below the sample material 610 and the reflector 640 will be located above the sample material 610. Reflector 640 on the sides and below the sources 630 can also enhance the neutron flux in the sample material 610. The detector 620, as described above, is capable of reacting with gamma rays and producing electrical pulses proportional to those gamma rays detected. The various components of the analyzer 600, in certain embodiments, are surrounded by shielding (not shown) to reduce the amount of radiation escaping from the analyzer 600. While other embodiments also utilize shielding material (not shown) between the neutron sources 630 and the detector 620 in order to minimize the number of gamma rays from the sources 630 that react with the detector 620. Certain embodiments utilize moderating material (not shown) above and/or below the sample material 610 to moderate neutrons to improve the chance of their absorption by the nuclei of the sample material 610 passing through the analyzer 600. The moderating material (not shown) can be any of the materials listed above or any other material that can be used to remove kinetic energy from the neutrons, and may be located between the sources 630 and the detector 620 as well.

In embodiments where multiple sources 630 are used and located on the same side of the sample material 610 as the detector 620, several advantages are achieved for both the embodiment illustrated in FIG. 6 and those previously described above. In such embodiments, the sources 630 can be located appropriately for the geometry of the analyzer 600 or for the type of material 610 being sampled or for the type of detector 620 being used to optimize the absorption of neutrons in the sample material 610 and the subsequent detection of gamma rays emitted by the sample material 610. Furthermore, in embodiments where the sources 630 are not located on an opposite side of the sample material 610 from the detector 620, the gamma rays from the sources 630 can effectively be shielded from detection without interfering with the paths of the neutrons to the sample material 610 or the paths of gamma rays to the detector. In fact, shielding that was formerly used to shield such gamma rays from detection can now be switched to shielding that is more effective in moderating the source neutrons to increase the probability of absorption in the sample material 610. Therefore, source gamma rays can be shielded effectively from detection, which would complicate analysis, without interfering with the detection of gamma rays emitted by the sample material, while improving absorption of neutrons in the sample material 610. These benefits can be seen in any embodiment described herein where the source 630 is not located colinearly with the sample material 610 and the detector 620.

In certain embodiments, the analyzer 600 is made up of one or more structures (not shown) for housing the components that make up the analyzer. A single housing may be used to house all of the components or multiple housings can be used. In one embodiment, the detector 620 is housed in a structure (not shown) that is separate from a structure that houses at least one other component, such as one or more of the sources 630.

In some embodiments, a pivot or hinge (not shown) can be used with whatever structure the detector 620 is housed within to rotate that housing structure about an axis. Such a pivot allows movement of the detector 620 to various positions or to a maintenance position to allow easy access to the detector 620 for maintenance or other reasons. In such embodiments, this structure can incorporate shielding or other material or any other components described above, which could make the structure very heavy, and the pivot can be placed near a center of gravity of that housing in order to facilitate ease of rotation of the housing.

G. Drill-Tailings Analyzer

Quarries and other mining sites are typically mapped for the ore of interest by drilling core samples and having them analyzed at a laboratory that is usually remote from the drilling site. Referring to the portable PGNAA materials analyzer 300 illustrated in FIG. 3 and the materials analyzer 500 of FIG. 5, these analyzers 300, 500 offer the opportunity of measuring the core samples immediately at the site where the drilling is done. By utilizing either of the analyzers 300, 500 at the drill site, the drill tailings can be analyzed as they are drilled in an expedient manner. The portable analyzer 300 allows core samples to be inserted into the analyzer measured at the drill site, and the materials analyzer 500 allows the drill tailings to continuously flow through the analyzer 500 for real-time continuous analysis of the tailings at the drill site. The depth of origin of each sample is readily determined from the drill depth for each sample analyzed or by measuring the bit height from which the sample was removed. The material analyzer 300/500 allows tailings from blast holes, holes drilled in the surface into which explosives are inserted, to be analyzed while a hole is being drilled, thereby mapping the holes while they are drilled and providing the opportunity of reducing the number of holes that need to be drilled and making the mapping and drilling processes more cost effective.

In this manner, the vertical profile of the composition of the ore can be determined for each drilling and the geographical location of the drill can be found by geographic mapping. Alternatively, a global position system indicating device, or GPS, can be implemented to accurately measure the geographic position of each drill. The analyses can be stored in a local computer (item 1000 of FIG. 1) or can be transmitted with the drill location and depth information to map mineral content in a drill site in three dimensions to a network communications system server as described below. The immediate mapping of material composition as a function of drill depth and geographic position offers many advantages for improving the economics of mining or any other geologic application. The three-dimensional material information can be transmitted to a remote station, as described below, for further processing.

H. Detector

Figure 7:
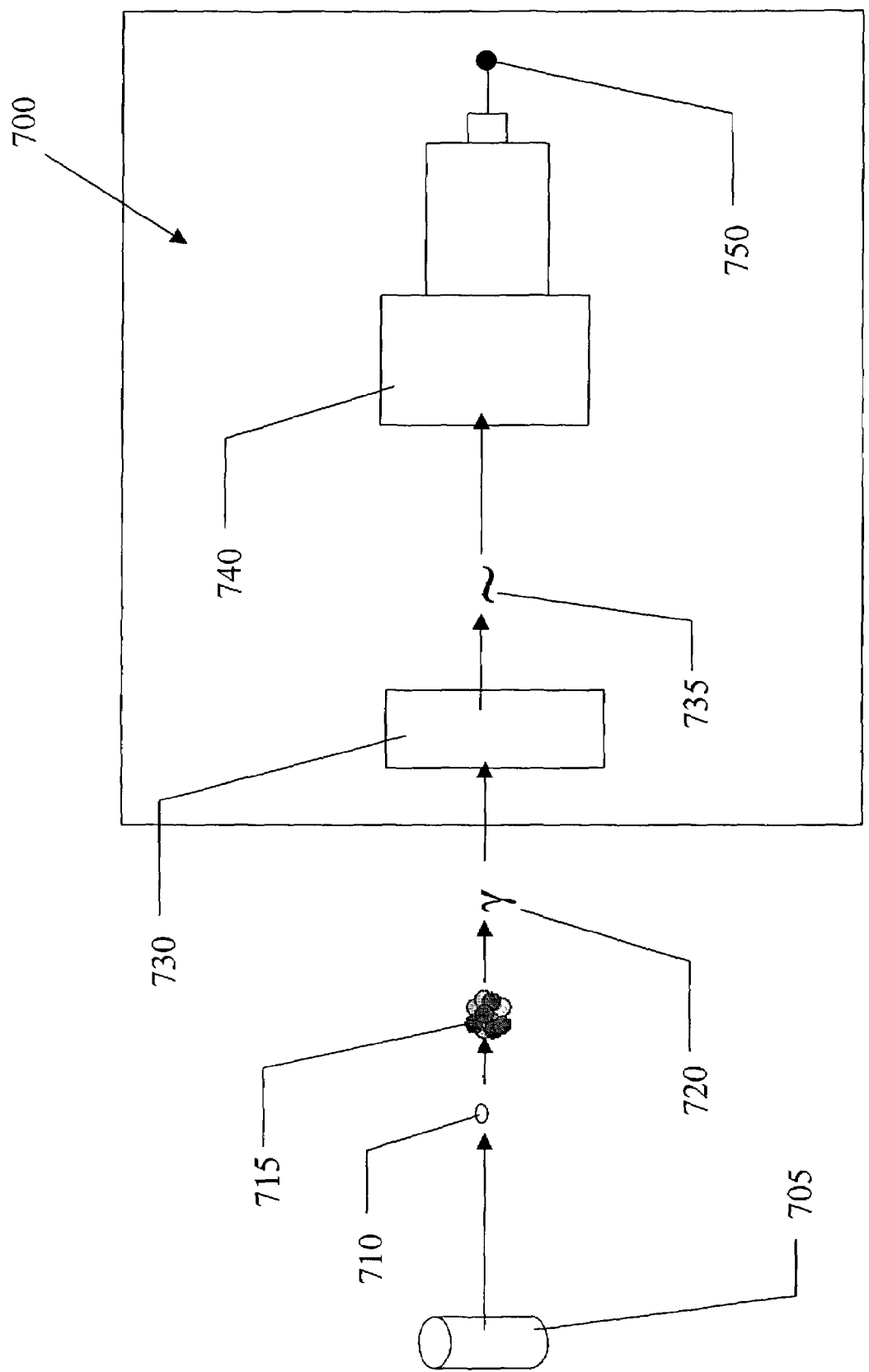
FIG. 7 is a schematic diagram of one embodiment of a detector for use in the materials analyzers of FIGS. 1 through 6.

FIG. 7 is a schematic representation of a detector 700 of one embodiment that can be used to detect the gamma radiation, or gamma rays, emitted by the material to be analyzed. In this illustration, a neutron source 705 emits neutrons 710, including a neutron 710 that is absorbed within the nucleus of an atom 715 that is part of a material sample in the analyzer (items 300 of FIG. 3 and 500 of FIG. 5). The atom 715 then emits absorption gamma rays 720 that are in the energy range from a few thousand electron volts to over ten million electron volts. The gamma rays 720 enter the detector 700, which converts the energy of a detected gamma ray into an electrical pulse that has an amplitude that is a measure of the energy of the detected gamma ray. Detectors that are commonly used to measure gamma rays in this energy range include a large scintillation crystal 730 coupled to a large photon counter 740. Common crystal sizes are six inches in diameter by six or seven inches long. Five-inch photomultiplier tubes are commonly used for the photon counter 740, however other types of highly sensitive light sensors can be used. A number of electronic components (not shown) that amplify the signal and convert it to digital format from analog for storing and processing are connected to the photon counter 740. The photon counter 740 provides pulse-amplitude gain, but the gain of photon counter 740 changes with time, temperature, excitation voltage and other conditions. The gain of electronic components connected to the photon counter 740 are much more stable than the photon counter 740, but can also drift with time and temperature.

Therefore, analyzers typically control the temperature of the detector 700 and the electronics associated with it with expensive heating/refrigeration units (not shown). Current analyzers also dynamically control the gain and offset by adjusting the detector excitation voltage or the electronics offset during the analysis, thereby calibrating the data provided by the detector before it is stored.

The need for temperature control and dynamic gain and offset control can, however, be reduced or eliminated. Gain and offset corrections, rather, can be made in the collected spectral data, or raw data, after collection and/or storage of that data as described below, rather than dynamically as it is being detected.

I. Data Collection and Analysis

1. Gain Control

Referring again to FIG. 1, the spectral data produced by the detector 140 is in the form of electrical pulses, which are stored with other relational information such as the time taken, the operator, sample identification information, or any other information the user sees fit to include. Each gamma ray detection event is called a count and produces an electrical pulse having a magnitude and a measure of the energy of the gamma ray. A portion of the processing of the data involves accumulating these counts into bins or "buckets" of uniform width in energy, where the contents of each bin indicates how many counts have arrived with energy between [E(center)−bucketwidth/2] and [E(center)+bucketwidth/2]. This processing is typically performed with a Multi-Channel Analyzer (MCA) device and the gain and offset of the detector and its preamplifier are controlled by constantly adjusting the magnitude of the excitation voltage of the photo-multiplier tube to keep the gamma-ray energies in the correct channels of the MCA. Alternatively, this processing can be performed by software as the spectral data is received at the computer (item 1000 of FIG. 1). The spectral data from the MCA can be adjusted periodically by software algorithms to keep the gamma-ray energies in the correct MCA channels. This can avoid the need for dynamic gain and offset control of the detector and the associated complexity.

One method of compensation comprises locating at least two, and preferably three or more, known spectral peaks and solving for the gain and offset by fitting a polynomial between the theoretical energy of each peak and the measured energy for each of those peaks. The collected spectral data is then resealed according to the polynomial determined in the last step via various "resampling" methods that are utilized in the field of audio waveform processing, including for example, using a FIR (finite impulse response) algorithm or filter, or use of a cubic spline interpolation algorithm or filter, as well as any other such resampling technique. Such resampling techniques are well known in audio waveform processing and voice sound waveform processing but have not been used before in the field of PGNAA and are exceedingly useful in this manner.

An advantage in correcting for gain and offset in the data, after it has been collected, is that the correction is actually more representative of each respective portion of data than such correction would be if "dynamic control," as it was referred to above, were used. In both cases, the need for a correction is determined from spectral data that has already been collected. In the method presented herein, the correction is applied to the portion of collected spectral data itself that was used to generate the correction, while dynamic control makes the correction in the next subsequent portion of spectral data that is read. By applying the correction derived from one data portion to a subsequent data portion, instead of to the portion from which the correction was derived, dynamic control develops some amount of jitter, or time-delay error, in the gain and offset of the total data set. Eliminating that jitter is equivalent to improving the energy resolution of the data set.

2. Pulse-Pileup Correction

Because the absorption of neutrons by the material being sampled and the subsequent emission of gamma rays are random events characterized by a Poisson distribution, the probability of two gamma rays being detected simultaneously is a function of the width of the resulting pulse and the average time between detection of any two gamma rays. When two gamma rays are detected simultaneously, the measured count rate is reduced by one count, known as count rate loss, and the amplitude of the resulting pulse is proportional to the sum of the energies of the two simultaneous gamma rays, known as pulse pileup. Pulse pileup distorts the measured data spectra and causes errors in the spectral analyses. As the count rate changes, this can also lead to gain shifts in prior art systems where dynamic gain control is determined by maintaining prominent spectral peaks centered at the correct energy channels for which they are known to be associated because pulse pileup broadens peaks in the direction of higher energy.

Pulse pileup across the data spectra can be calculated if the pulse shape, the circuit timing and the average count rate are known. When starting with a spectrum that has been collected, the piled up spectra for any higher count rate can be easily calculated. However, it is extremely difficult to determine the appropriate un-piled spectra from collected piled up spectra, the reverse calculation. The reason for this is that, the pileup function is not easily inverted mathematically. For spectral data, it is further complicated by not knowing whether an energy count is the correct energy or a piled up energy from the addition of two lower energies. In one embodiment of an analyzer 100 of FIG. 1, a spectrum of data is collected and the average count rate is determined for that spectrum of data. That spectrum is assumed for a moment to be free from pulse pileup, and a calculation is made to determine what the theoretical piled up spectrum would be at that count rate for that spectrum. This is calculated from the collected spectrum as if it were free of pulse pileup from the probabilities of any particular energy level piling up at that count rate, which are known because the total counts at that energy have been measured in collecting the spectrum. Since the piled up spectrum is not a great deal different from the same spectrum that is free of pileup, the calculated pileup for the collected spectrum is very nearly the same as the pileup that is included in the collected spectrum. The difference between the collected spectrum and the calculated, theoretically piled up spectrum is then subtracted from the original collected spectrum and the resulting spectrum is very close to a spectrum that is free of pileup for that material. Though not perfect, the resulting spectral data are much closer to the ideal spectrum than is accomplished by other current methods of removing the pulse pileup. It is noteworthy that this procedure not only removes piled-up pulses but also adds the counts back into the original spectral peaks that lost the counts in the piling-up process. Many approaches for eliminating pulse pileup throw away any piled-up pulses that are identified.

Piled up spectra are the source of several problems in spectral analyses in PGNAA analyzers. Pulse pileup changes the shape of the collected spectra and, thereby, causes direct errors in the deconvolution of the spectra for determining the masses of the elements that are present in the material. In addition, the probability of a pulse of a certain energy piling up on another pulse is proportional to the fraction of the total pulses that are of that energy. Since there are more low-energy pulses than high-energy pulses, more of the pileup occurs with low-energy pulses, which has the additional effect of broadening every spectral peak. Anything that broadens the spectral peaks, adversely affects the precision and accuracy of the spectral deconvolution. Beyond that, because pulse pileup broadens spectral peaks only toward the higher energy side of the peak, it also changes the effective energy of the centroid of the spectral peak. For systems that perform dynamic gain control based on measuring the centroids of known spectral peaks, a different gain is established for every count rate and calibrations become count rate dependent, thus requiring periodic re-calibration as neutron sources decay or when new sources are added to an analyzer. Thus, analysis accuracy and stability are improved and the need for re-calibration as count rates change is avoided with pulse pileup correction.

3. Data Collection

Referring again to FIG. 1, in some embodiments, a materials analysis system stores raw spectral data collected from a material under test directly to fixed or removable memory, as opposed to performing a computational analysis as the data arrives and saving the computational results to memory. In certain embodiments, the raw spectral data is stored to disk either before or after removing pulse pileup, and the analysis system performs a materials analysis for each time interval. The time interval can be any interval, such as one to five minutes, within some bulk data span, such as up to 24 hours or more, upon request by a user. By storing raw data and performing analysis of stored data, a system permits re-analysis of data using different parameters at any time, and decouples the CPU-intensive analysis process from the real-time data collection process, thereby decreasing system complexity and increasing system reliability.

The data collection process of one embodiment includes the above-mentioned steps of acquiring data pulse samples from an analog-to-digital converter, storing that data to a disc or database, correction of nonlinear energy response of the detector and electronics, and removal of pulse pileup. Some embodiments will only store the data after either, or both, the correction of non-linear response and removal of the pulse pileup are completed while other embodiments will not perform either of these steps prior to storage. Once the data has been collected and stored, selected intervals of the data can be sampled and analyzed via an analysis process.

Figure 8:
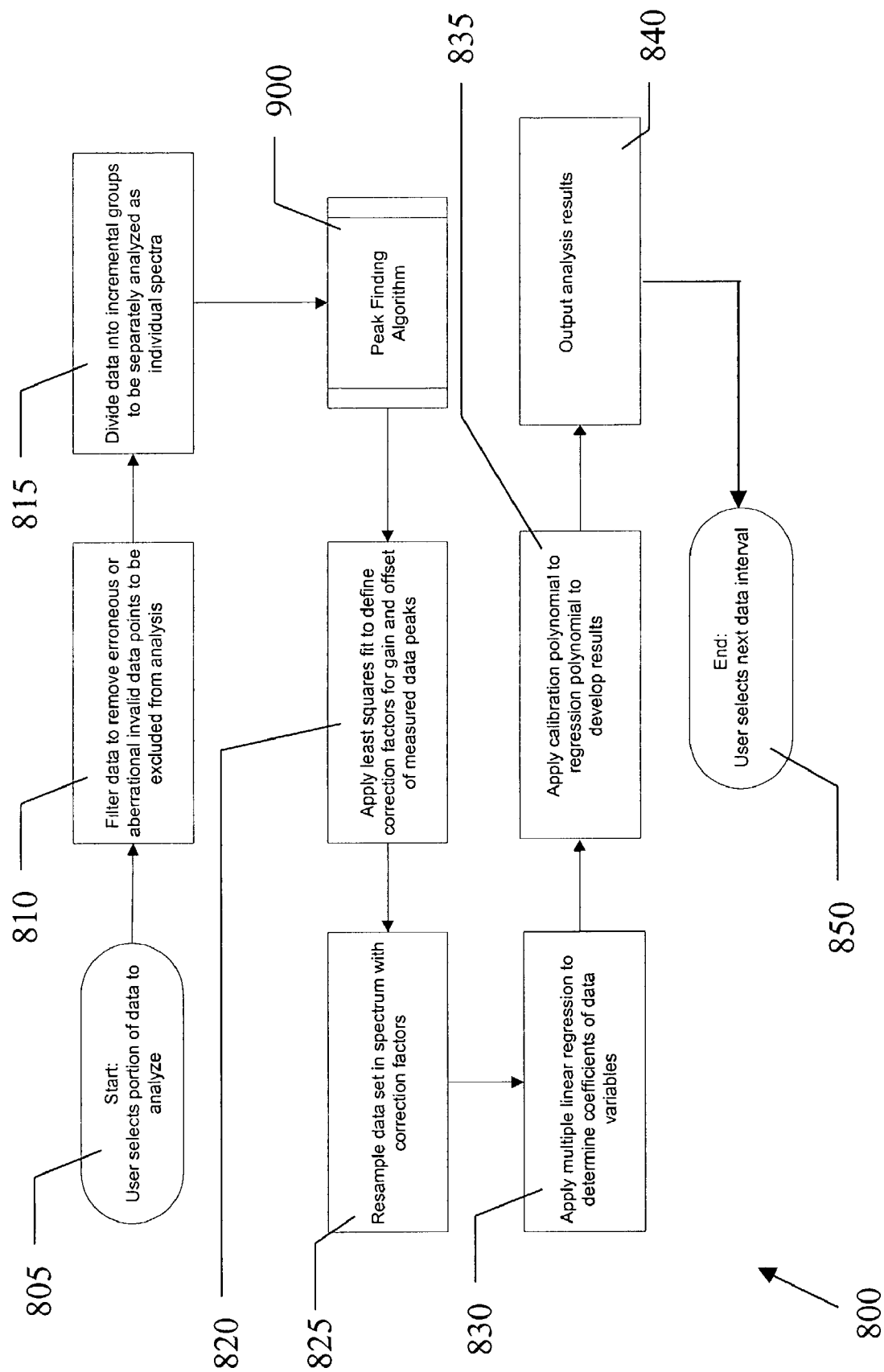
FIG. 8 is flow chart illustrating one embodiment of a process for analyzing data in a PGNAA analysis system.

One embodiment of a process that can be used to analyze the collected data is illustrated in FIG. 8. The data analysis process illustrated in FIG. 8 begins at state 805 where a user selects data to be analyzed. In many embodiments, the data will be selected in time increments over some period to be analyzed such as from five minutes to twenty four hours, although shorter or longer periods can be used. The process then moves to filter state 810 where invalid data or data to be otherwise excluded is filtered out of the process 800. The user defines some parameters for determining which data points are to be filtered out of the rest of the process 800. These may be energy levels that are clearly not representative of any materials that can be in the sample or are representative of gamma rays known to have come from the source (item 120 of FIG. 1, among others) rather than from the sample. Many other criteria for filtering the data are common in the art and can be used. The process 800 then moves to state 815 where the data is divided into increments of time, the length of which are selected by the user. In some embodiments, the increments of time will be from one to five minutes in duration and all of the data pulses collected during that time will be analyzed as one spectrum by aggregating all of the data pulses of each energy level across the spectrum. The process 800 then moves to a subprocess 900.

At subprocess 900, a peak finding algorithm is utilized to find at least two recognizable energy peaks across the spectrum. Certain embodiments find three recognizable energy peaks while other embodiments find more than three recognizable energy peaks across the spectrum. The method for finding these peaks is described below with reference to FIG. 9. After the recognizable energy peaks are located, the process 800 moves to state 820 where a least squares fit is performed to define a polynomial from each peak to a theoretical peak location, which is used as a reference of where that peak should be. The polynomial will determine the adjustment factors to be applied to the measured spectral peaks to correct any gain and offset errors. Referring again to FIG. 8, the process 800 then moves to state 825 where the data for the spectral interval is resampled as described above with the correction factors for the gain and offset settings to correct the sampled data to the response set.

When the resampled data spectrum is determined by process state 825, the process 800 then moves to process state 830 where a multiple linear regression analysis is performed to fit the spectral data to the response set. This provides coefficients and error estimates for each elemental member of the response set including the material sampled as well as the detector baseline reading and other response set items. Certain channels, or discrete energy levels, that are not useful to the linear regression solution are identified and provided with an exceptional error estimate, or sigma value, for processing by the regression analysis of process state 830, thus effectively eliminating the undesired channels from the computations. The process 800 then moves to a process state 835 where a calibration polynomial is applied to the regression solution polynomials to develop the final results. Calibration polynomials are commonly used in data-reduction algorithms for conversion of data to recognizable measurement units. A calibration is required to develop the data-reduction equation or mathematical function that characterizes the relationship between the raw coefficients returned by the linear regression procedure and the actual mass percentage composition of the material being analyzed. Polynomial equations are a common functional form of calibration where first order polynomials are used if the relationship between the coefficients and composition is linear, and are higher order if the relationship is more complex. The process 800 then moves to process state 840 where the final results for the analysis of each subinterval are output from the process 840. The output from the process 800 can be in many forms, such as a data file, a graphical output representation, or any other output form. The process 800 then ends at ending state 850. This process 800 is then repeated for each interval of time in the set of data selected by the user to provide analysis results for all of the data within the selected time period.

Figure 9:
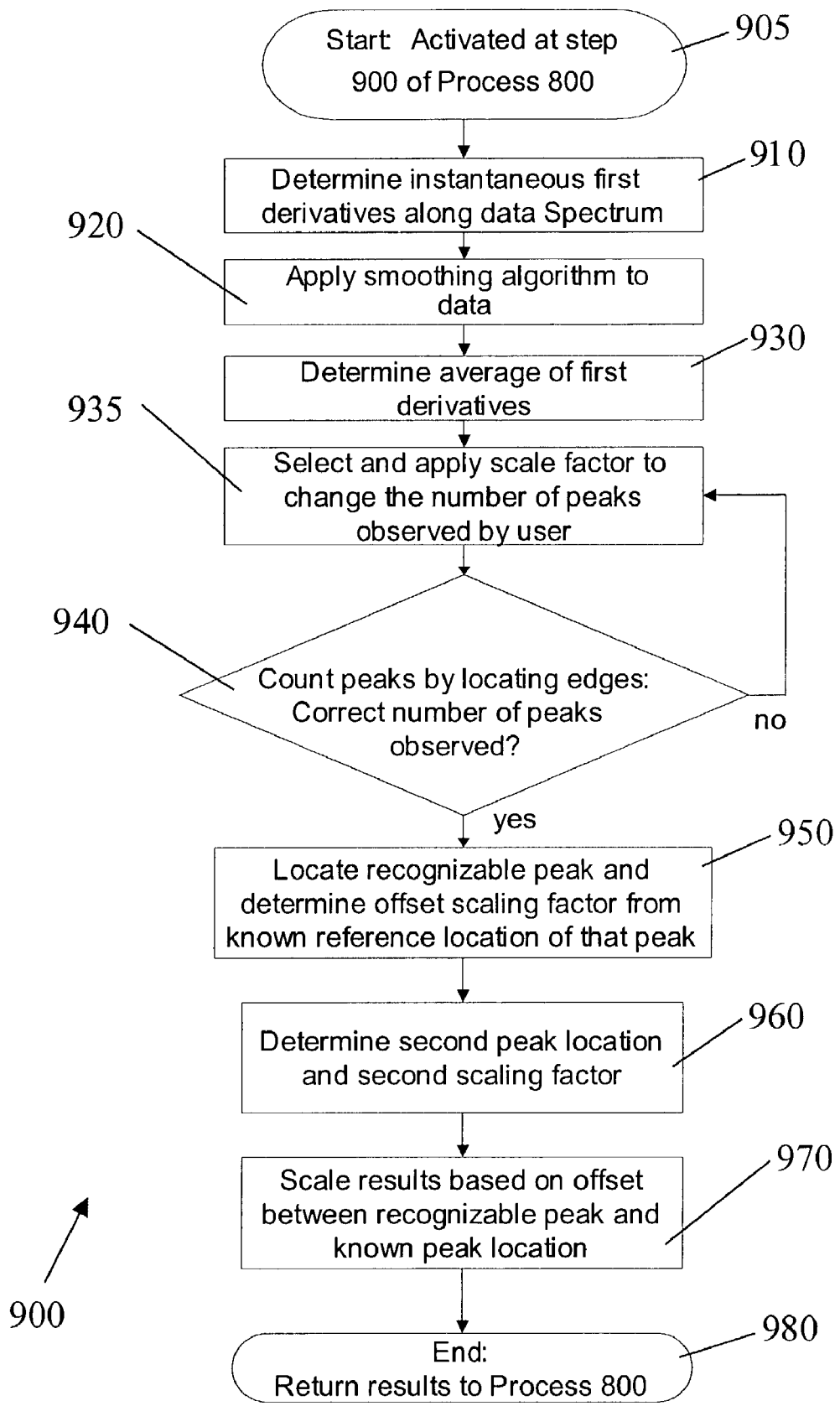
FIG. 9 is a flow chart illustrating one embodiment of a process for finding data peaks for use in the process illustrated in FIG. 8.

Referring to FIG. 9, the subprocess 900 of FIG. 8 is described for a peak finding algorithm that is utilized to find at least two recognizable energy peaks across the data spectrum. As mentioned before, certain embodiments find three recognizable energy peaks while other embodiments find more than three recognizable energy peaks across the spectrum. The subprocess 900 begins at a starting state 905 when directed by the process 800 illustrated in FIG. 8. The subprocess 900 then moves to state 910 where the first derivative of the data spectrum is taken all along the spectrum. The subprocess 900 then moves to state 920 where the data spectrum and derivatives are smoothed to remove noise from the spectral data. Smoothing algorithms are very common in statistical data manipulation and any smoothing algorithm can be used to smooth the data and derivatives of this subprocess 900. This step is optional, however, and certain embodiments omit it for simplicity.

The subprocess 900 then moves to state 930 where the average of the derivatives across the spectrum is determined. The subprocess 900 then moves to state 935 where an arbitrary scale factor is chosen. The subprocess 900 then moves to state 940 where the "edges" of each peak are located by taking a product of the scale factor and the average of the derivatives found in state 930 and comparing the product to the first derivatives along the spectrum. The edges of the peaks are the parts of the derivative of a count or pulse where the first derivative exceeds the product. This illustrates the number of peaks expressed by the scaling factor selected and applied at state 935. If there are too many or too few peaks, the process will return to state 935 where another scale factor is chosen and applied. The peakfinding scale factor is normally adjusted by reducing it if too few peaks are seen, and increasing it if too many peaks are seen. This allows more or fewer peaks to be recognized. Furthermore, the desired number of peaks may also vary depending on the amount of detail visible in the spectrum. In a high-resolution spectrum, there are intrinsically more spectral features present and it is usually necessary to allow more peaks to be found in order to locate the chosen reference peaks. Conversely, in a relatively low-resolution spectrum the targeted number of peaks must be kept lower to avoid seeing undesired noise peaks. A smaller or larger scale factor is chosen to get fewer or more peaks, respectively, although some embodiments can use algorithms having an inverse relation. When the desired number of peaks are visible such that some recognizable peaks can be ascertained, the subprocess 900 moves to state 950. At state 950 a very recognizable peak is located, such as that produced by a gamma ray emitted from a hydrogen nucleus, although those gamma rays emitted by other atoms could be used as well. A predicted channel offset is then computed from the distance from the recognizable peak to another nearby recognizable peak, such as from the main hydrogen peak to the first escape peak of hydrogen, by multiplying the difference in peak energies by the nominal channel scaling in channels per unit energy. It is helpful if the second peak is fairly close to the first peak since gain corrections of several percent are not uncommon, making it difficult to unambiguously predict the location of a second peak that may be several MeV away. If the nearby second peak is indeed found to be present at the predicted offset, a preliminary gain scaling factor and offset are then computed from the observed energy difference between the first and second peaks, by fitting a polynomial to the two peak locations. This gain scaling factor and offset are then used in turn to predict the location of one or more additional peaks at higher energies, typically in the 5 MeV range although any visible peak could be used. The subprocess 900 then moves to state 960 where the offset factor determined at state 950 is used to search for a peak at a higher energy, such as in the 5 MeV range. The peak produced by iron can be used, but any other element producing a second energy peak can also be used. The location of the third peak, and any other peaks, if subsequently located, are used in a linear regression calculation to obtain a best-fit polynomial (gain and offset) relating the observed spectral peaks to their theoretical locations. The subprocess 900 then moves to a state 970 where the offset and gain scaling factors determined at states 950 and 960 are applied to the data spectrum to correct the peak locations in the spectrum as a whole. The subprocess 900 then moves to an ending state 980 where the corrected results are returned to process 800.

J. Computer

Figure 10:
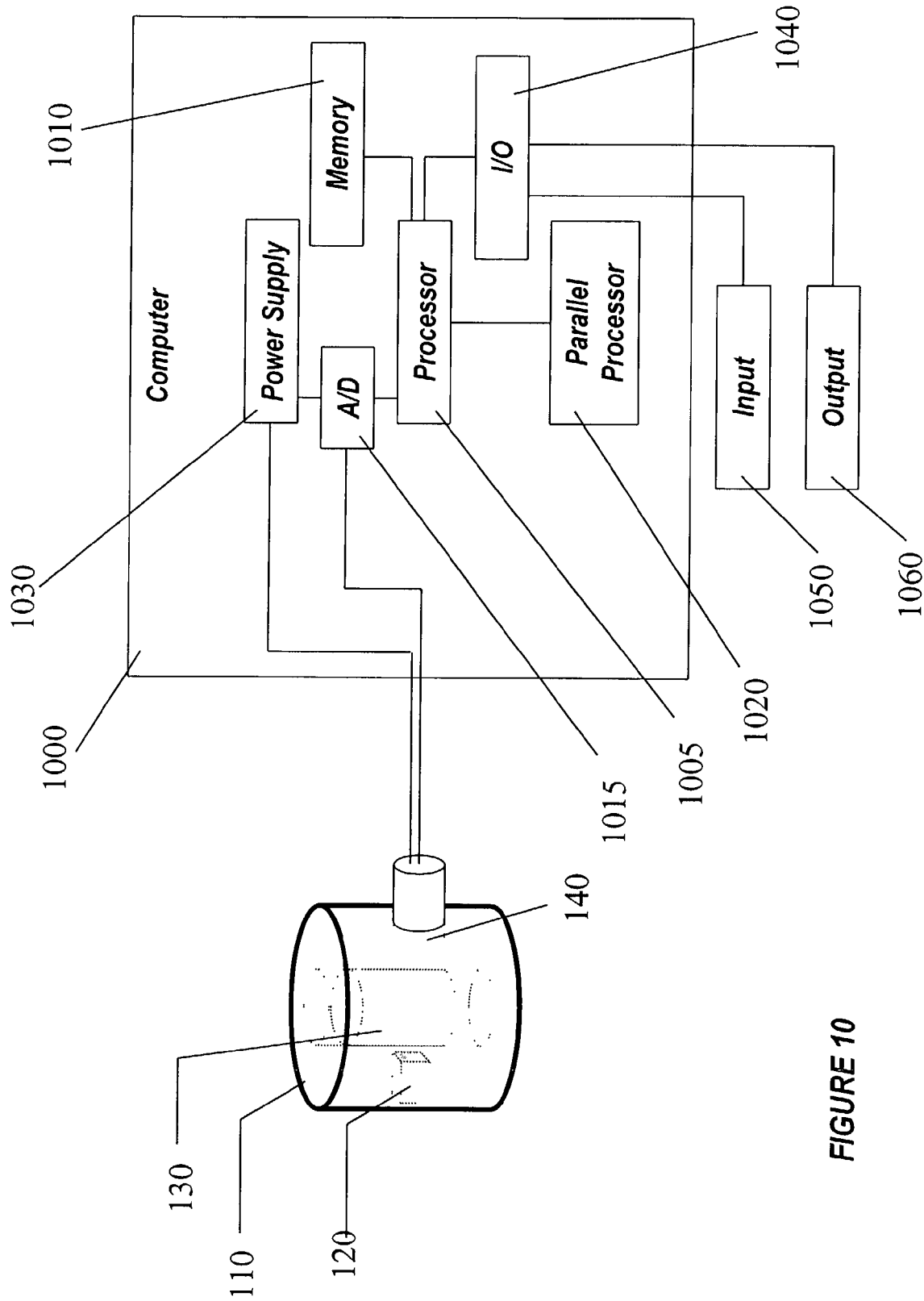
FIG. 10 is a schematic diagram of one embodiment of a computer or data processor used in a PGNAA system.

Referring to FIGS. 1 and 10, an embodiment of the computer 1000 or data processing station is illustrated that is capable of receiving data pulses from the analyzer 110, storing the data, and processing the data as described above. Certain embodiments store the raw data to conserve resources that are utilized in the data analysis process described above, while other embodiments perform the data analysis prior to storage. In the following description, the computer 1000 is assumed to have all connectivity necessary to fulfill and embody the functions that will be described including all communication ports and connections as well as any required conductors and bus-work. The computer 1000 is comprised of various modules 1005–1060. As can be appreciated by one of ordinary skill in the art, each of the modules 1005–1060 comprises various sub-routines, procedures, definitional statements, and macros. Each of the modules 1005–1060 can be separately compiled and linked into a single executable program, or alternatively could be compiled into a plurality of executable programs. Therefore, the following description of each of the modules 1005–1060 is used for convenience to describe the functionality of the computer 1000. Thus, the processes that are undergone by each of the modules 1005–1060 may be arbitrarily redistributed to one of the other modules, combined together in a single module, or made available in a shareable dynamic link library. Furthermore, the organization of the various functional modules in the structure illustrated in FIG. 10 is merely for illustrative purposes only and the modules can be organized in any other way and can be located in different structures than the one illustrated here. In some embodiments, many of the components can be located in part of the housing of the analyzer 110, or in other structures.

Still referring to FIGS. 1 and 10, the main operative module of the computer 1000 is the processor 1005. The various illustrative logical blocks, modules, and circuits described in connection with the embodiments disclosed herein may be implemented or performed with or by the processor 1005, which can be a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor 1005 may be a microprocessor, but in the alternative, the processor 1005 may be any processor, controller, microcontroller, or state machine. The processor 1005 may also be implemented as a combination of computing devices, e.g., a combination of a DSP and a microprocessor, a plurality of microprocessors, one or more microprocessors in conjunction with a DSP core, or any other such configuration. Specifically, the processor 1005 may be any conventional general purpose single or multi-chip microprocessor such as a Pentium® processor or its progeny, an AMD Athlon® or its progeny, an Itanium® 64-bit processor or its progeny, a MIPS® processor, a PowerPC® processor or its progeny, or an ALPHA® processor or its progeny. In addition, the processor 1005 may be any conventional special purpose microprocessor such as a digital signal processor as described above.

Additionally, computer 1000 has a memory 1010 for storing data and other information. The memory 1010 may include any storage medium including, but not limited to, RAM memory, DRAM memory, SDRAM memory, flash memory, ROM memory, EPROM memory, EEPROM memory, registers, hard disk, a removable disk, a CD-ROM, a DVD-ROM, or any other form of storage medium. An exemplary storage medium, or memory 1010, is coupled to the processor 1005 such that the processor 1005 can read information from, and write information to, the memory 1010. In the alternative, the memory may be integral with the processor 105. The processor 1005 and the memory 1010 may reside in an ASIC. The computer 1000 receives the data from the analyzer 110 in the form of analog electrical pulses that are converted into digital information by an analog to digital converter (A/D) 1015. Again, the A/D 1015 can be integral with the processor in some embodiments.

Still referring to FIGS. 1 and 10, the processor 1005 performs complex and resource strenuous analysis functions on the data received from the analyzer 110, and some embodiments utilize a parallel processor or coprocessor 1020, such as a floating point accelerator or any other parallel processor, to assist in the performance of many of these analytical functions. Both the computer 1000 and the analyzer 110 utilize electrical power to perform their respective functions and a power supply 1030 is provided to supply them. The power supply 1030 can be located in the computer or in one or more separate housings and can be two integrated supplies or can be two separated supplies, one each for the computer 1000 and the analyzer 110. In many embodiments, the computer 1000 has an input/output module (I/O) 1040 for controlling information coming into and out of the computer 1000. The I/O 1040 receives commands that operate the computer 1000, which in turn operates the analyzer 110, from an input source 1050. For example, the I/O 1050 can be a keyboard, trackball, pen and stylus, mouse, digitizer, or voice recognition system. The I/O 1050 can also be a touch screen associated with an output device 1060. The user may respond to prompts on the display by touching the screen. The user may enter textual or graphic information through the input device that represents command subroutines to be executed by the computer 1000. The output signals from the computer 1000 are sent to an output device 1060, or system, for use by the operator. The output device 1060 can be a printer, a plotter, a display for graphic output, or an audio output for sound or voice synthesis, or it can be a connection to a server or a network, such as that described below, or it can be any other form as required by the operator.

K. Network

Figure 11:
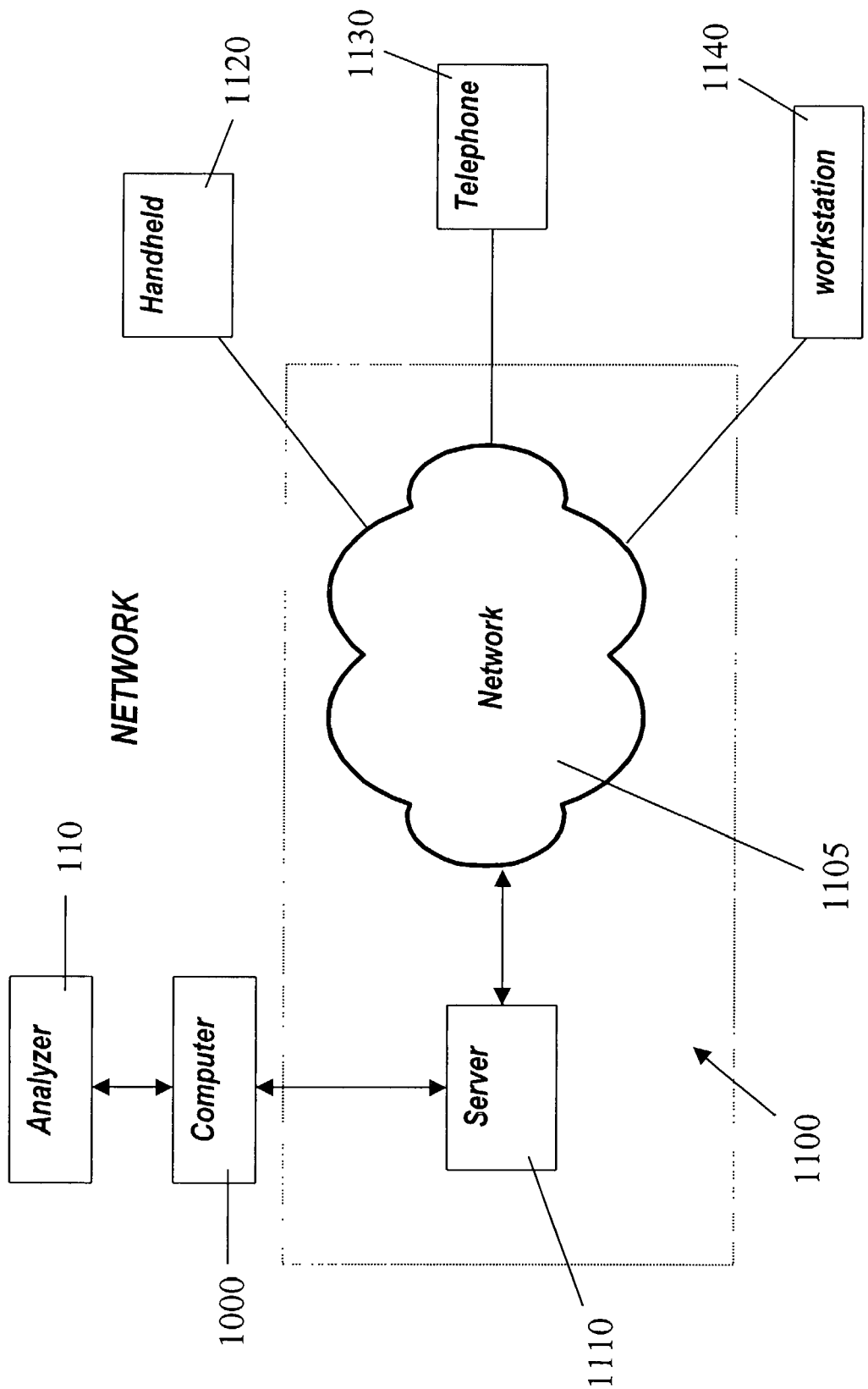
FIG. 11 is a schematic diagram of one embodiment of a network that can be used in a PGNAA system.

Referring to FIGS. 1, 10 and 11, one embodiment of a PGNAA analysis system includes a network system 1100 for remotely controlling analysis and detection operations or for remotely accessing stored data. The network system 1100 has a network 1105 that is accessed by the computer 1000 and other workstations 1120, 1130, 1140 for communicating information between the analyzer 110 and its associated computer 1000 and a number of remote workstations 1120, 1130, 1140. The network 1105 may include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI), Asynchronous Transfer Mode (ATM) or any other type. Note that computing devices may be desktop, server, portable, hand-held, set-top, telephone, or any other desired type of configuration. As used herein, the network 1105 includes network variations such as the public Internet, a private network within the Internet, a secure network within the Internet, a private network, a public network, a value-added network, an intranet, satellite-based networks, and the like, whether the connectivity of the network be via electrical connector, fiber-optic, point-to-multi/point laser, radio wave, microwave, or any other connection method. While FIG. 11 illustrates a particular architecture, it should be recognized that the modules 1000, 1100–1140 are arranged in this manner as an example of one embodiment and any arrangement can be used to allow each function described herein to be performed locally at a computer 1000 or remotely from any number of various workstations 1120, 1130, 1140. For instance, some or all of the components of the computer 1000 can be located remotely at any one or all of the workstations 1120, 1130, 1140. Those of skill in the art will recognize the network 1100 illustrated in FIG. 11 can encompass many various embodiments that can fulfill the functions described herein.

The computer 1000, or one or more of the remote workstations 1120, 1130, 1140, reads pulse energies from the hardware of the analyzer 110 and writes the data to a memory 1010. As was mentioned above, the memory 1010 can be in the computer 1000 itself or can be located remotely from the computer 1000 in any of the workstations 1120, 1130 or anywhere else on, or connected to, the network 1105. Data analysis by the processor 1005 can be initiated by a user initiating a command on a remote workstation 1120, 1130, 1140 that makes a request to a server 1110 that can be any type of communications or network server capable of allowing the storage and processing resources of the system to be shared among the various workstations 1120, 1130, 1140. The request triggers an analysis process via any means, whereby servers, such as web servers or other network servers for example, can invoke one or more external processes in the processor 1005 by any protocol. The server 1110 can invoke the process(es) for example, and not limitation, with any of one or more common or standard protocol programs such as by CGI or PHP external programs, or by any special purpose interfacing system and routines. The external process initiates the processor 1005, which computes the analysis results for a plurality of subintervals. In some embodiments, the external process initiated by the network 1100 can operate the analyzer 110 and perform the analysis directly.

Some embodiments allow access to the computer 1000 via the network 1105, or the components of the computer 1000 can be located across the network 1105, for performing all operations remotely, including retrieving data from the analyzer 110, storing the data in the memory 1010, retrieving data from the memory 1010, selecting and analyzing a particular data set, or any other function. Those of skill in the art will recognize that the network 1105 can be accessed by standard workstations 1140, or by handheld computing devices 1120 such as PDAs, by telephones or radios 1130 by setting up proper server and/or client interface protocol. For instance, some embodiments allow access via telephone lines 1130 for recognizing certain voice operated or numeric tone-based commands. Other embodiments allow access to the server by radio or infrared communication with handheld units 1120. While still other embodiments, also allow access by any other network protocol such as TCP/IP, ISDN, T1, DSL, or any other protocol. Thereby, the analyzer can be operated from any location having network connectivity, such as telephone, Ethernet or Internet for example, to the analysis system. In addition to expanded location access, several workstations 1120, 1130, 1140 can view analysis results at the same time without further implementation effort.

Additionally, referring to FIGS. 1, 5 and 11, the communication link (not separately identified) from the analyzer 110 to the computer 1000, or from the computer 1000 to the server 1110, or from the server 1110 to the network 1105, may be wireless, thereby allowing the portable analyzer 300 to be remotely located for remote analysis. For instance, the portable analyzer 300 can be connected to a portable computer 1000 in remote contact with the network 1105. The server 1110 can be located anywhere within the network 1105 and can be remotely located with the computer 1000 and in remote communication with the network 1105. Such embodiments allow a portable analyzer 300 to provide data from the field as the site to be surveyed is being sampled in real time with or without location information embedded with the data. This reduces the time necessary for taking samples to a laboratory for such analysis. The remote analyzer 110 and computer 1000 can either provide full data, or analyzed data results, or merely provide feedback to the server 1110 or the network 1105 when materials of interest are located. Such a system can be used in mining, quarrying, or any other geological surveying. The communications configuration described here for the portable analyzer 300 is also applicable to the material analyzer 500 and any other embodiment described herein.

Still referring to FIGS. 10 and 11, one embodiment of the computer 1000 system uses an industry standard ATX type motherboard in a rackmount, tower, or desktop enclosure, with single or multiple Athlon® or Pentium® CPUs 1005, 256 MB of RAM and 20–60 GB of hard disk 1010. I/O 1040 to and from the analyzer 110 is accomplished through a standard PCI bus interface card attached to the motherboard that reads the spectrum pulses and controls the detector. In some embodiments, the computer 1000 operates under the Linux® operating system and utilizes an Apache web server to generate the user interface. Alternatively, the computer 1000 could run a Microsoft Windows® operating system and use a Microsoft IIS web server. In these embodiments, the analyzer 110 may be operated via any web browser or browsing device, including but not limited to, Microsoft Internet Explorer, Netscape, Mozilla and Konqueror. Such web browsers may be co-resident on the computer 1000 or reside remotely on workstations 1120, 1130, 1140, or on a handheld device, or on any device with an operative web browser and network connectivity to the computer 1000. In addition to analyzer operational functions, the network interfaces of the computer 1000 can also be utilized for secure remote maintenance, field service and monitoring, software upgrading, administrative, and other related purposes via any standard protocol, such as, for example, SSH (Secure SHell), FTP (File Transfer Protocol) and HTTP (HypterText Transfer Protocol).

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A substance analyzer for identifying characteristics of a sample of a substance, comprising:
   a sample volume adapted to contain the sample of said substance;
   a source adapted to emit neutrons;
   a first composition of material adapted to moderate, shield and reflect the neutrons, wherein said neutrons emitted by the source are absorbed by the sample, and wherein the sample then emits at least one gamma ray;
   a gamma radiation detector located adjacent to the sample volume and adapted to develop electrical signals in response to detection of the at least one emitted gamma ray;
   a housing comprising an outer container and an inner container located within the outer container, wherein said inner container is adapted to contain the sample volume, the source, the detector, and the first composition of material; and
   a second composition of material disposed between the inner container and the outer container and adapted to absorb neutrons.

2. The substance analyzer of claim 1, wherein the outer container comprises a commercial storage drum.

3. The substance analyzer of claim 2, wherein the inner container comprises a drum that is smaller than the outer container.

4. The substance analyzer of claim 3, wherein a gap is formed between the inner container and the outer container, and wherein the gap contains the second composition of material.

5. The substance analyzer of claim 4, wherein the second composition of material comprises a mixture of water extended polyester and neutron absorbing material that is initially liquid in form and solidifies over time.

6. The substance analyzer of claim 5, wherein the inner container is removed after the second composition of material solidifies.

7. The substance analyzer of claim 5, wherein the neutron absorbing material comprises at least one substance selected from the group consisting of: boron, indium, cadmium, gadolinium, hafnium, samarium, europium, dysprosium, rhodium, erbium, thulium, iridium, platinum, or gold.

8. The substance analyzer of claim 4, wherein the second composition of material comprises a pourable shielding material.

9. The substance analyzer of claim 8, wherein the pourable shielding material comprises water extended polyester.

10. The substance analyzer of claim 3, wherein the inner container is made of polyethylene.

11. The substance analyzer of claim 1, wherein the housing is generally cylindrical.

12. A substance analyzer for identifying characteristics of a sample of a substance, comprising:
  a source adapted to emit neutrons;
  a sample volume adapted to contain the sample of the substance and having an open entrance end and an open exit end, wherein the sample passes through the sample volume as it is analyzed;
  a first composition of material adapted to moderate, shield and reflect the neutrons emitted by the source, wherein neutrons emitted by the source are absorbed by the sample, wherein the sample then emits at least one gamma ray;
  a gamma radiation detector adapted to develop electrical signals in response to detection of the at least one gamma ray;
  a housing comprising an outer container and an inner container located within the outer container, wherein said inner container is adapted to contain the sample volume, the sample, the source, the detector, and the first composition of material; and
  a second composition of material disposed between the inner container and the outer container and adapted to absorb neutrons.

13. The substance analyzer of claim 12, wherein said outer container comprises a commercial storage drum.

14. The substance analyzer of claim 13, wherein the inner container comprises a smaller drum.

15. The substance analyzer of claim 14, wherein a gap is formed between the inner container and the outer container, and wherein the gap contains the second composition of material.

16. The substance analyzer of claim 15, wherein the second composition of material comprises a mixture of water extended polyester and neutron absorbing material that is initially liquid in form and solidifies over time.

17. The substance analyzer of claim 16, wherein the inner container is removed after the second composition of material solidifies.

18. The substance analyzer of claim 16, wherein the neutron absorbing material comprises at least one substance selected from the group consisting of: boron, indium, cadmium, gadolinium, hafnium, samarium, europium, dysprosium, rhodium, erbium, thulium, iridium, platinum, or gold.

19. The substance analyzer of claim 15, wherein the second composition of material comprises a pourable shielding material.

20. The substance analyzer of claim 19, wherein the pourable shielding material comprises water extended polyester.

21. The substance analyzer of claim 14, wherein the inner container is made of polyethylene.

22. The substance analyzer of claim 12, wherein said housing is generally cylindrical.

23. A bulk material analyzer for analyzing material carried on a conveyor having first and second sides, the analyzer comprising:
  at least one source located in operable proximity to one of the first and second sides of the conveyor and adapted to emit neutrons;
  a composition of material adapted to moderate, shield and reflect the neutrons, wherein said neutrons emitted by the source are absorbed by the bulk material, and wherein the bulk material then emits at least one gamma ray; and
  a gamma radiation detector located in operable proximity to one of the first and second sides of the conveyor and adapted to develop electrical signals in response to detection of the at least one emitted gamma ray, wherein the at least one source and the detector are located on the same side of the material being analyzed.

24. The analyzer of claim 23, wherein the at least one source is located in a separate structure from the detector.

25. The analyzer of claim 24, further comprising a pivot adapted to rotate a detector housing about an axis.

26. The analyzer of claim 23, wherein the conveyor is a conveyor belt system.

27. The analyzer of claim 23, wherein the conveyor is a conveying tube.

28. The analyzer of claim 23, wherein the first side is below the conveyor and the second side is above the conveyor.

29. The analyzer of claim 23, further comprising at least two sources.

30. The analyzer of claim 23, wherein the at least one source is housed in a first structure, and wherein the detector is housed in a second structure.

31. The analyzer of claim 23, wherein the composition of material further comprises a reflector material adapted to direct the neutrons onto the material being analyzed.

32. The analyzer of claim 23, further comprising a pivot adapted to rotate the detector.

33. A material analyzer for detecting the elemental composition of a bulk material comprising:
  a radioactive source adapted to emit neutrons;
  a sample volume having an open entrance end and an open exit end and adapted to convey a flow of cement clinker;
  a first composition of material adapted to moderate, shield and reflect radiation emitted by the source, wherein the cement clinker absorbs neutrons emitted by the source and then emits at least one gamma ray;
  a gamma radiation detector adapted to develop electrical signals in response to detection of the at least one gamma ray;
  a housing comprising an outer container and an inner container located within the outer container, wherein said inner container is adapted to contain the source, the detector, the sample volume, the flow of cement clinker and the first composition of material, wherein the flow of cement clinker enters the sample volume via the entrance end and exits the sample volume via the open exit end; and
  a second composition of material disposed between the inner container and the outer container and adapted to absorb neutrons.

34. The material analyzer of claim 33, wherein the generally cylindrical sample volume is a pipe extending substantially longitudinally through the analyzer.

35. The material analyzer of claim 34, wherein the material being analyzed is a flow of geological survey materials.

36. The material analyzer of claim 35, wherein at least a portion of the pipe extending through the active region of measurement is made of reactor-grade zirconium.

37. The material analyzer of claim 34, wherein the material analyzed is a flow of mining tailings.

38. The material analyzer of claim 34, wherein the pipe is made of Acrylonitrile-Butadiene-Styrene.

39. The material analyzer of claim 34, wherein the pipe is made of iron.

40. A material analyzer for detecting the elemental composition of a coal slurry comprising:
- a source of neutrons;
- a sample volume having an open entrance end and an open exit end adapted to convey a flow of the coal slurry;
- a composition of material adapted to moderate, shield and reflect neutrons emitted by the source, wherein neutrons emitted by the source are absorbed by the coal slurry, which then emits at least one gamma ray;
- a gamma radiation detector adapted to develop electrical signals in response to detection of the at least one gamma ray emitted by the coal slurry;
- a housing comprising an outer container and an inner container located within the outer container, wherein the outer and inner containers are configured so as to define an entrance side and an exit side and wherein the inner container is adapted to contain the source, the detector, the sample volume, the flow of the coal slurry and the composition of material, wherein the sample volume extends within the housing from the entrance to the exit, and wherein the coal slurry enters the sample volume via the entrance end and exits the sample volume via the exit end; and
- a second composition of material disposed between the inner container and the outer container and adapted to absorb neutrons.

41. The material analyzer of claim 40, wherein the outer container is a first commercial storage drum.

42. The material analyzer of claim 41, wherein the inner container is a second commercial storage drum that is smaller than the first commercial storage drum.

43. The material analyzer of claim 42, wherein the inner container is made of polyethylene.

44. The material analyzer of claim 42, wherein a gap is formed between the inner container and outer container, and wherein the gap contains shielding material.

45. The material analyzer of claim 40, wherein the sample volume is generally rectangular.

46. A system for three-dimensional surveying of a concentration of various elements in the earth, comprising:
- a portable material analyzer adapted to analyze the concentration of elements;
- a drill adapted to extract a plurality of material samples from the earth;
- means for determining depth within the earth of the origin of each of the material samples by measuring bit height from which the sample was removed; and
- means for correlating material analyses to a respective drill depth of each of the plurality of material samples.

47. The system of claim 46, wherein the correlating means is a drill depth gage.

48. The system of claim 46, wherein the system further comprises a geographical map adapted to correlate a drill location of each of the plurality samples with a geographical location, and wherein each of the plurality of samples are analyzed to produce a data set representing the concentration of the elements in each of the samples.

49. A method of surveying the elemental composition of a portion of the earth, comprising:
- drilling a hole in the surface of the earth from which a material sample is extracted;
- determining a geographical position of the hole;
- measuring drill bit height from which the sample was removed so as to determine a depth from which the sample was extracted;
- analyzing one or more characteristics of the sample using a portable material analyzer located substantially near the drill site; and
- correlating a set of analysis data with the depth and geographical position of the sample.

50. The method of claim 49, wherein the survey is performed in real-time as the analyzing step is performed substantially at the time the sample is taken.

51. A substance analyzer for identifying characteristics of a sample of a substance, comprising:
- a source of neutrons;
- a sample volume adapted to contain the sample of the substance;
- a first composition of material adapted to moderate, shield and reflect any neutrons emitted by the at least one source, wherein neutrons emitted by the at least one source are absorbed by the sample, and wherein the sample then emits at least one gamma ray;
- a gamma radiation detector adapted to develop electrical signals in response to detection of the at least one gamma ray emitted by the sample;
- a housing comprising an outer container and an inner container located within the outer container, wherein said inner container is adapted to contain the source, the detector, the sample volume, the sample and the composition of material; and
- a load cell adapted to develop an electrical signal corresponding to a mass of the sample contained in the sample volume.

52. A substance analyzer for identifying characteristics of a sample of a substance, comprising:
- a source of neutrons;
- a sample volume adapted to contain the sample of the substance;
- a composition of material adapted to moderate, shield and reflect any neutron radiation emitted by the source, wherein neutrons emitted by the source are absorbed by the sample, and wherein the sample then emits at least one gamma ray;
- a gamma radiation detector adapted to develop electrical signals in response to detection of the at least one emitted gamma ray;
- a housing having a generally longitudinal axis extending in a substantially vertical direction and adapted to contain the source, the detector, the sample volume, the sample and the composition of material; and
- an elevator adapted to displace the sample in the sample volume generally parallel to the longitudinal axis of the housing.

53. A substance analyzer for identifying characteristics of a sample of a substance, comprising:
- a source of neutrons;
- a sample volume adapted to contain the sample of the substance;
- a composition of material adapted to moderate, shield and reflect any neutron radiation emitted by the source, wherein neutrons emitted by the source are absorbed by the sample, and wherein the sample then emits at least one gamma ray;

a gamma radiation detector adapted to develop electrical signals in response to detection of the emitted at least one gamma ray;

a generally cylindrical housing comprising an outer container and an inner container located within the outer container, wherein said inner container is adapted to contain the source, the detector, the sample volume, the sample and the composition of material; and a rotator, adapted to rotate the sample in the sample volume relative to the inner container.

54. A portable substance analyzer for identifying the characteristics of a sample of a substance, comprising:

a source of neutrons;

a sample volume adapted to contain the sample of the substance;

a composition of material adapted to moderate, shield and reflect any neutron radiation emitted by the source, wherein neutrons emitted by the source are absorbed by the sample, and wherein the sample then emits at least one gamma ray;

a gamma radiation detector adapted to develop electrical signals in response to detection of the at least one emitted gamma ray;

a generally cylindrical housing comprising an outer container and an inner container located within the outer container, wherein said inner container is adapted to contain the source, the detector, the sample volume, the sample and the composition of material, wherein the housing is generally less than 50 inches tall and generally less than 40 inches in diameter; and a second composition of material disposed between the inner container and the outer container and adapted to absorb neutrons.

* * * * *